(12) United States Patent
Wang et al.

(10) Patent No.: US 8,017,104 B2
(45) Date of Patent: Sep. 13, 2011

(54) LARGE STOKE SHIFT DYE USED FOR OPTICAL IMAGING

(75) Inventors: Ruizheng Wang, Rochester, NY (US); John W. Harder, Rochester, NY (US); David A. Stegman, Churchville, NY (US); William J. Harrison, Pittsford, NY (US); Hans F. Schmitthenner, Rush, NY (US)

(73) Assignee: Carestream Health, Inc., Rochester, NY (US)

( * ) Notice: Subject to any disclaimer, the term of this patent is extended or adjusted under 35 U.S.C. 154(b) by 600 days.

(21) Appl. No.: 11/712,531

(22) Filed: Feb. 28, 2007

(65) Prior Publication Data

US 2008/0206886 A1    Aug. 28, 2008

(51) Int. Cl.
*A61K 49/00* (2006.01)
*G03C 1/00* (2006.01)
*C07D 209/04* (2006.01)

(52) U.S. Cl. ........ 424/9.1; 430/281.1; 430/944; 528/469

(58) Field of Classification Search .............. 430/281.1, 430/944; 548/469; 424/9.1
See application file for complete search history.

(56) References Cited

U.S. PATENT DOCUMENTS

| | | | |
|---|---|---|---|
| 4,520,110 A | 5/1985 | Stryer et al. |
| 4,542,104 A | 9/1985 | Stryer et al. |
| 4,666,862 A | 5/1987 | Chan |
| 4,707,454 A | 11/1987 | Hendrix |
| 4,981,977 A | 1/1991 | Southwick et al. |
| 5,286,486 A | 2/1994 | Payne et al. |
| 5,326,692 A | 7/1994 | Brinkley et al. |
| 5,453,505 A | 9/1995 | Lee et al. |
| 5,464,741 A | 11/1995 | Hendrix |
| 5,498,875 A | 3/1996 | Obremski et al. |
| 5,532,129 A | 7/1996 | Heller |
| 5,565,322 A | 10/1996 | Heller |
| 5,569,587 A | 10/1996 | Waggoner |
| 5,573,909 A | 11/1996 | Singer et al. |
| 5,580,733 A | 12/1996 | Levis et al. |
| 5,627,027 A | 5/1997 | Waggoner |
| 5,646,264 A | 7/1997 | Glazer et al. |
| 5,763,189 A | 6/1998 | Buechler et al. |
| 5,767,267 A | 6/1998 | Glazer et al. |
| 5,808,044 A | 9/1998 | Bruch et al. |
| 5,809,185 A | 9/1998 | Mitchell |
| 5,849,489 A | 12/1998 | Heller |
| 5,877,310 A | 3/1999 | Reddington et al. |
| 6,008,373 A | 12/1999 | Waggoner et al. |
| 6,043,025 A | 3/2000 | Minden et al. |
| 6,048,690 A | 4/2000 | Heller et al. |
| 6,090,552 A | 7/2000 | Nazarenko et al. |
| 6,127,134 A | 10/2000 | Minden et al. |
| 6,130,094 A | 10/2000 | Waggoner et al. |
| 6,133,445 A | 10/2000 | Waggoner et al. |
| 6,162,603 A | 12/2000 | Heller |
| 6,168,892 B1 | 1/2001 | Ohara et al. |
| 6,204,068 B1 | 3/2001 | Soini et al. |
| 6,232,075 B1 | 5/2001 | Williams |
| 6,238,931 B1 | 5/2001 | Buechler et al. |
| 6,255,083 B1 | 7/2001 | Williams |
| 6,306,607 B2 | 10/2001 | Williams |
| 6,327,074 B1 | 12/2001 | Bass et al. |
| 6,366,793 B1 | 4/2002 | Bell et al. |
| 6,416,953 B1 | 7/2002 | Heller |
| 6,667,830 B1 | 12/2003 | Iketaki et al. |
| 6,762,048 B2 | 7/2004 | Williams |
| 6,844,154 B2 | 1/2005 | Landers |
| 6,887,662 B1 | 5/2005 | Alajem et al. |
| 6,911,310 B2 | 6/2005 | Heller |
| 6,951,761 B2 | 10/2005 | Star et al. |
| 6,969,615 B2 | 11/2005 | Knezevic et al. |
| 6,982,146 B1 | 1/2006 | Schneider et al. |
| 7,008,768 B1 | 3/2006 | Fornace, Jr. et al. |
| 7,045,319 B2 | 5/2006 | Hanna |
| 7,081,336 B2 | 7/2006 | Bao et al. |

FOREIGN PATENT DOCUMENTS

| | | |
|---|---|---|
| EP | 1 065 250 | 12/2004 |
| JP | 2004-252189 | * 9/2004 |
| WO | 93/23492 | 11/1993 |
| WO | 97/40104 | 10/1997 |
| WO | 99/51702 | 10/1999 |
| WO | 02/32464 | 4/2002 |
| WO | 2006/019755 | 2/2006 |
| WO | 2006/019775 | 2/2006 |

OTHER PUBLICATIONS

Muirhead et al., Biotechnology, vol. 3, (Apr. 1985), pp. 337-356.
Ozmen et al., Tetrahedron Letters 41, (2000), pp. 9185-9188.
Mujumdar et al.Bioconjugate Chem., vol. 4, (1993),pp. 105-111.
Mishra, et al., Chem Rev., (2000), 100, pp. 1973-2011.
Oi et al., J. Cell Bio., vol. 93, Jun. 1982, pp. 981-986.
Stryer et al., Energy Transfer: A Spectroscopic Ruler, Proc. Nat'l Acad. Sci., USA, 58, 1967, pp. 719-726.
Haughland et al., Dependence of the Kinetics of Singlet-Singlet Energy Transfer on Spectral Overlap, PNAS 1969;63, pp. 23-30.
Gorelenko et al., Photonics of Bichromophores Based on Laser Dyes in Solutions and Polymers, Exp. Technik der Physik 37, 1989, pp. 343-346.
Saito et al., Appl. Phys. Lett., 56, 1990, 811-813.
F.M. Hamer, Heterocyclic Compounds—Cyanine Dyes and Related Compounds,(Chapter VIII—Symmetrical and Unsymmetrical Heptamethincyanines, Including those with Substituents on the Chain; Polymethincyanines), John Wiley & Sons, New York & London , 1964, pp. 244-269.
D.M. Sturmer, Heterocyclic Compounds Specia Topics in heterocyclic chemistry, John Wiley & Sons, New York & London, 1977,pp. 485-515.

* cited by examiner

*Primary Examiner* — Paul V. Ward

(57) ABSTRACT

The present invention relates to a diagnostic contrast agent comprising a water dispersible, near-infrared tricarbocyanine, enamine-functionalized dye having a Stoke shift of greater than 50 and represented by five general formulae. The present invention also relates to a method for making a dye-conjugate utilizing the novel dye and a method of identifying a biological compound using the novel dye conjugate.

14 Claims, 1 Drawing Sheet
(1 of 1 Drawing Sheet(s) Filed in Color)

LARGE STOKE SHIFT DYE USED FOR OPTICAL IMAGING

FIELD OF THE INVENTION

The present invention relates to fluorescent dyes for in-vitro and in-vivo imaging applications.

BACKGROUND OF THE INVENTION

Fluorescent dyes are valuable reagents for the analysis and separation of molecules and for the labeling and detection of biomolecules for in-vitro and in-vivo for research in development of new drugs, pharmacology, pathology and disease detection. Flow cytometry can be used to detect fewer than 10,000 fluorescein dye labeled cells (Muirhead, Horan and Poste, BIOTECHNOLOGY, 3, 337-356 (1985)).

For in-vivo studies, specifically sequenced peptides can be labeled with fluorescent dyes and imaged as circulated through blood and tissue and by concentrated in tumors and other disease sites. Stem cells can be labeled with dyes to follow their development. Nucleotides can be covalently attached to dyes to allow DNA, RNA, and genetic studies. For in-vitro studies, fluorescent dyes can be covalently bound to antibodies and used in proteins assays as Western Blot. Brightly fluorescent dyes have demonstrated utility as labeling reagents for a variety of biological applications, eg U.S. Pat. Nos. 4,981,977 to Southwick, et al. (1991); 5,286,486 to Waggoner et al. (1993); 5,569,587 to Waggoner (1996); 5,627,027 to Waggoner (1997); 5,808,044 to Brush, et al. (1998); 5,877,310 to Reddington, et al. (1999); 6,008,373 to Waggoner, et al. (1999); 6,043,025 to Minden, et al. (2000); 6,127,134 to Minden, et al. (2000); 6,130,094 to Waggoner, et al. (2000); 6,133,445 to Waggoner, et al. (2000); also WO 97/40104, WO99/51702, WO 01/212624, and EP 1 065 250 A1; and TETRAHEDRON LETTERS 41, 9185-88 (2000); all of the above incorporated by reference.

Nevertheless many carbocyanine dyes are known to share certain constraints for the above purposes. One constraint is the absorbtion and emission characteristics of the fluorescent dye, since many ligands, receptors, and materials in the sample under test, e.g. blood, tissue, bone, will fluoresce and interfere with an accurate determination of the fluorescence of the dye. This phenomenon is called autofluorescencse or background fluorescence.

Another consideration is the ability to conjugate the fluorescent dye to ligands and receptors and other biological and non-biological materials and the effect of such conjugation on the fluorescent dye. In many situations, conjugation to another molecule may result in a substantial change in the fluorescent characteristics of the fluorescent dye and in some cases, substantially destroy or reduce the quantum efficiency of the fluorescent dye. It is also possible that conjugation with the fluorescent dye will inactivate the function of the molecule that is labeled.

Another concern is whether there is non-specific binding of the fluorescent dyes to other compounds or container wall, either by themselves or in conjugation with the compound to which the dye is attached.

In addition certain desired sulfoalkyl derivatives of the reactive carbocyanine dyes are difficult to prepare, indicated in Cy3 and Cy5 variants by Waggoner and colleagues in BIOCONJUGATE CHEM., 4, 105-109 (1993). Cyanine dyes also have very strong tendency to self-aggregate which can significantly reduce the fluorescence quantum yields as described by Mishra, et al., CHEM REV., 100, 1973 (2000). The self-aggregation often limits the amount of dye that can be attached to the desired biomolecule which in turn limits the brightness that can be achieved per conjugate. Another concern of carbocyanine dyes is their sensitivity to destruction by light and oxygen such that handling, storage and testing of the dyes and their conjugates often requires protecting them from light.

Since all of these factors must be considered in design a useful dye for bio-applications, there is a desire to make the dye as useful as possible in the equipment that measures the dyes. One consideration is the emissive capability of the dye often measured by its quantum efficiency. Another consideration is the light absorbing capability of the dye often measured by its extinction coefficient, which should be as large as possible.

Typical fluorescent dyes in use as labeling reagents for biological molecules such as xanthenes, dipyrrometheneboron difluorides, rhodamines and carbocyanines commonly have Stoke shifts of less than about 30 nm. Here the Stoke shift is defined as the difference between the fluorophore's peak excitation and peak emission wavelengths. Because the optimum wavelength of the exciting light is close to close to the peak emission light, dyes with small Stoke shifts require precise excitation and emission filters to eliminate or reduce interference. Furthermore, the customary use of excitation and emission bandpass filters means that only a fraction of the available excitation and emission light may be practically utilized for dyes possessing a small Stoke shift resulting in a diminution of the fluorescence signal. Fluorescent materials that incorporate bright fluorescent dyes with increased Stoke shift permit maximum utilization of the available excitation and emission light, resulting in a greater fluorescence signal.

Another advantage of fluorescent materials with large Stoke shifts is that they can be more easily detected in the presence of other fluorescent materials. For example, immunoassays are typically carried out in body fluids which contain may endogenous fluorescent molecules, such as bilins, flavins and drugs. Since the vast majority of interfering fluorescent materials have relatively short Stoke shifts, the use of a fluorescent label that emits at a wavelength far greater than its excitation wavelength makes the label easier to distinguish from background fluorescence, since its fluorescent signal is emitted at a wavelength at which most background fluorescence is minimal.

A third advantage of fluorescent materials with large Stoke shifts is their usefulness in detecting multiple analytes in a single sample using a single excitation wavelength. Using two or more different fluorescent labels, each of which can be excited at a particular wavelength, the emission peaks of the different labels are detected at different wavelengths, where each emission spectrum is characteristic of a single analyte. In order to successfully accomplish this, the emission peaks of the fluorescent labels must be well-separated from each other so the correction factors between the various dyes are minimized. Fluorescent materials with a large Stoke shift can be used in combination with fluorescent materials with a smaller Stoke shift where both materials excite at the same wavelength, but emit at different wavelengths, giving multiple signals that can be resolved using optical filters or monochromators.

Unfortunately, fluorescent compounds useful as labeling agents that have Stoke shifts of 50-100 nm, or more, as well as high fluorescence efficiency and emission wave lengths of greater than 500 nm required for detectability are relatively rare (Haughland, Fluorescein Substitutes for Microscopy and Imaging, Optical Microscopy for Biology pp. 143-57, 1990). The magnitude of the Stoke shift in fluorescent dyes has been found to be generally inversely proportional to the high absorbance needed to ensure a strong fluorescence signal. Fluorescent dyes in use as labelling reagents for biological molecules commonly have Stoke shifts of less than about 30 nm.

The lack of suitable fluorescent dyes with large Stoke shifts has led to the development and use of protein-based fluorophores known as phycobiliproteins as labels (e.g. U.S. Pat. Nos. 4,520,110 and 4,542,104). Like other fluorophores, they have been covalently attached to beads and macromolecules (see, for example, Oi et al., J. Cell Bio., 93, 981, 1982). These large bilin-containing molecules have the desirable characteristics of very high extinction coefficients and they use internal energy transfer between multiple, unlike, covalently-linked fluorophores to accomplish a relatively large Stoke shift. They have the disadvantage of poor chemical stability, poor photostability, limited long wavelength emission capability, bulky molecular size (MW>100,000 Daltons) and relatively high cost. Furthermore, only a few proteins of this type are known and one cannot select or appreciably adjust their spectral properties. In an effort to improve the fluorescent emission efficiency of phycobiliproteins without significantly increasing their molecular size, they have been covalently coupled to the fluorescent dye Azure A (U.S. Pat. No. 4,666,862).

In studies of energy transfer between pairs of covalently linked dyes, it has been shown that the efficiency of energy transfer between two fluorescent dyes is inversely proportional to the sixth power of the distance between the two interacting molecules, consistent with Förster's theory (Stryer and Haughland, Energy Transfer: A Spectroscopic Ruler, Proc. Nat'l Acad. Sci., USA, 58, 719, 1967). The reference suggests that the percentage of measurable energy transfer can be used to measure the distance separating the covalently linked fluorophores in the 10 to 60 Å range. A subsequent paper (Haughland et al., Dependence of the Kinetics of Singlet-Singlet Energy Transfer on Spectral Overlap, PNAS, 63, 23, 1969) reported that intramolecular singlet energy transfer also depends on the magnitude of spectral overlap integral between the emission spectrum of the donor dye and the excitation (absorbance) spectrum of the acceptor dye.

It is known that covalent coupling of a pair of fluorophores in accordance with Förster's theory can result in a fluorescent dye with a larger Stoke shift than either of the individual dyes (e.g. Gorelenko et al., Photonics of Bichromophores Based in Laser Dyes in Solutions and Polymers, Exp. Technik der Physik 37, 343, 1989). This approach, although reportedly effective in increasing the Stoke shift, requires complex synthetic procedures to chemically couple the two dyes together and are limited by the number and location of available reactive sites. The process of carrying out the necessary synthetic procedures to attach multiple dyes sufficiently close together and in the proper spatial and orientational configuration to undergo substantial energy transfer would be exceedingly difficult, if not impossible. Furthermore, covalently linked molecules typically have sufficient freedom of movement that significant collisional deactivation of the excited state occurs, leading to loss of energy by vibrational relaxation rather than by fluorescence. Energy transfer with resultant wavelength shifting has also been described for mixtures of dyes in lasing solutions (e.g. Saito et al., Appl. Phys. Lett., 56, 811, 1990).

The concept of utilizing Förster resonance energy transfer between two or more particle-incorporated fluorescent dyes to achieve an enhanced Stoke shift has been described in U.S. Pat. No. 5,326,692 by Brinkley et al. and U.S. Pat. No. 6,238,931 B1 by Buechler et al.

WO2006/019775 by Pandey, et al., discloses a compound having preferential localization in tumor tissue relative to normal tissue, a preferential electromagnetic absorbtion at a wavelength between about 660 and 900, and a fluorescence at a wavelength shifted from the preferential absorbtion by at least 30 nm. This is accomplished by the combination of two chromophores, one of which is a weakly absorbing tetrapyrrole compound the such that the maximum excitation energy is not shifted from the maximum emission peak by greater than 50 nm WO2002/32464 by Achilefu, describes a benzindole of the formula:

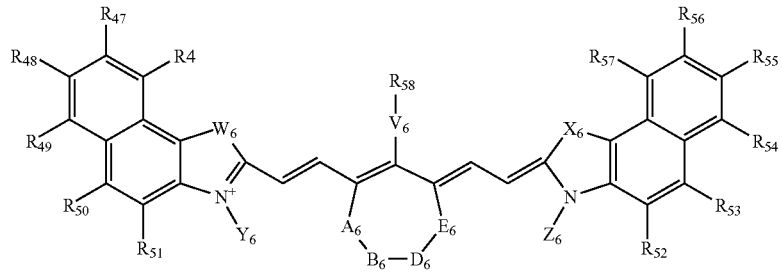

This structure varies from the current invention in that A6, B6, D6, E6 may together form a 6 or 7 membered carbocyclic ring or a 6 or 7 membered heterocylic ring optionally containing one or more oxygen nitrogen or sulfur atoms. V6 is a single bond or selected from a group of —O—, —S—, —Se—, —NRa, where Ra is selected from a list of substituents. There is no disclosure of large Stoke shift dyes in this application.

According to WO93/23492 "Unfortunately, fluorescent compounds useful as labeling reagents that have Stoke Shifts of 50-100 nm or more, as well as high fluorescence efficiency and emission wavelengths of greater than 500 nm required for detectability are relatively rare. Fluorescent dyes in-vivo as labeling reagents for biological molecules, such as xanthenes, bipyrrometheneboron difluorides, rhodamines and carbocyanines commonly have Stoke Shifts of less than about 30 nm. To solve this problem, multiple fluorescent dyes were immobilized in a polymeric matrix. However the attachment of polymeric matrix of fluorescent dyes to biological molecules requires increased synthetic complexity and the polymeric materials can have adverse effects on biodistribution, clearance, cellular uptake, and cytotoxicity.

U.S. Pat. No. 5,573,909 relates to methods for labeling or detecting one or more target materials using surface coated fluorescent microparticles with unique characteristics. The unique microparticles have at least two components: an external substance or coating that is selective for each target material and an internal mixture of multiple fluorescent dyes. The mixture of dyes is a series of two or more fluorescent dyes having overlapping excitation and emission spectra allowing efficient energy transfer from the excitation wavelength of the first dye in the series, and resulting in fluorescent microparticles with a desired effective Stoke shift, transfer through the dyes in the series and re-emitted as an optical signal at the emission wavelength of last dye in the series, resulting in a desired effective Stoke shift for the microparticle that is controlled through selection of appropriate dyes. The unique microparticles are combined with a sample thought to contain the target material(s), so that the microparticles label the target materials. The sample is then optionally illuminated, resulting in fluorescence of the microparticles that is used to detect one or more target materials.

The invention relates to methods of labeling target materials using fluorescent microparticles having a surface coating that is selective for the target materials.

U.S. Pat. No. 5,326,692 relates to microparticles incorporating a series of two or more fluorescent dyes having overlapping excitation and emission spectra allowing efficient energy transfer from the excitation wavelength of the first dye in the series, transfer through the dyes in the series and re-emitted as an optical signal at the emission wavelength of last dye in the series, resulting in a desired effective Stoke shift which is controlled through selection of appropriate dyes. The novel fluorescent microparticles are useful in applications such as the detection and analysis of biomolecules, such as DNA and RNA, that require a very high sensitivity and in flow cytometric and microscopy analytical techniques.

PROBLEM TO BE SOLVED

There remains a need for an improved fluorescent dye for in-vitro and in-vivo imaging.

SUMMARY OF THE INVENTION

The present invention relates to a diagnostic contrast agent comprising a water dispersible, near-infrared tricarbocyanine, enamine-functionalized dye having a Stoke shift of greater than 50 and represented by the following five general formulae:

General Formula I

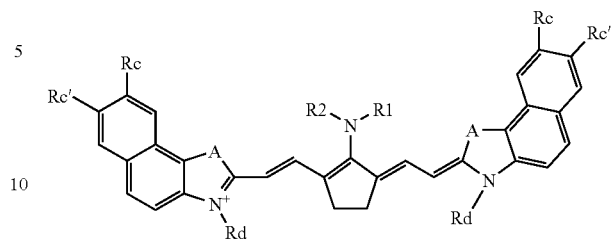

Wherein R1 and R2 are substituted alkyl and may form a ring and at least one of R1 or R2 is a linking group selected from a list of COOH, NH2, maleimide, thiol, isocyanate, isothiocyanate, disulfide, alkynyl, azidoyl, or trialkoxysilane; A is NRa, S, O, Ra—C—Rb, wherein Ra and Rb are substituted or unsubstituted alkyl groups capable of forming a ring; Rc is hydrogen or SO3-, aryl, alkyl, alkoxy, or halogen; Rd is alkyl or (CH2)nSO3- where n=2 to 4, General Formula II

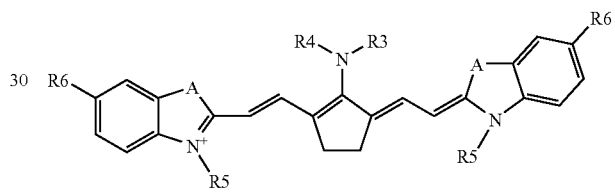

Wherein R1 and R2 are substituted alkyl and are capable of forming a ring, and at least one of R1 or R2 is a linking group selected from a list of COOH, NH2, maleimide, thiol, isocyanate, isothiocyanate, disulfide, alkynyl, azidoyl, or trialkoxysilane; A is NRa, S, O, Ra—C—Rb, wherein Ra and Rb are substituted or unsubstituted alkyl groups capable of forming a ring; Rc is hydrogen or SO3-, aryl, alkyl, alkoxy, or halogen; Rd is alkyl or (CH2)nSO3- where n=2 to 4, General Formula III

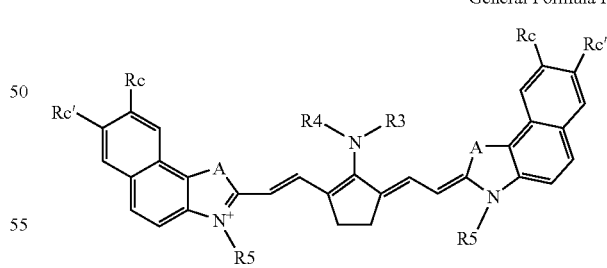

Wherein A is NRa, S, O, Ra—C—Rb; R3, R4, Ra, and Rb are substituted or unsubstituted alkyl capable of joining together to form a ring; R6 is a SO3-; R5 is substituted alkyl and at least one of the substituents is selected from a list of OH, NH2, COOH, maleimide, thiol, isocyante, isothiocyanate, disulfide, alkynyl, azidoyl, or trialkoxysilane;

General Formula III

Wherein A is NRa, S, O, Ra—C—Rb; R3, R4, Ra, and Rb are substituted or unsubstituted alkyl capable of joining together to form a ring; at least one of Rc and Rc' is a SO3-; R5 is substituted alkyl and at least one of the substituents is selected from the group consisting of OH, NH2, COOH, maleimide, thiol, isocyante, isothiocyanate, disulfide, alkynyl, azidoyl, or trialkoxysilane; Rc is hydrogen or SO3-, aryl, alkyl, alkoxy, or halogen; and General Formula V

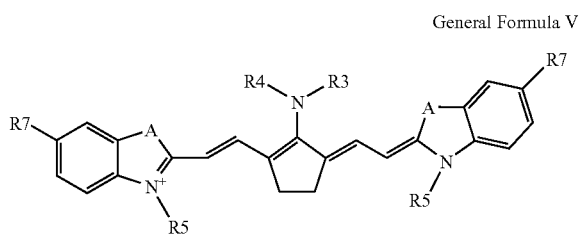

Wherein A is NRa, S, O, Ra—C—Rb; R3, R4, Ra, and Rb are substituted or unsubstituted alkyl capable of joining together to form a ring; R7 is a COOH; R5 is substituted alkyl and contains a SO3- group. The present invention relates to a method of making diagnostic contrast agent conjugate comprising providing a water dispersible, near-infrared tricarbocyanine, enamine-functionalized dye having a Stoke shift of greater than 50 and represented by the following five general formulae:

General Formula I

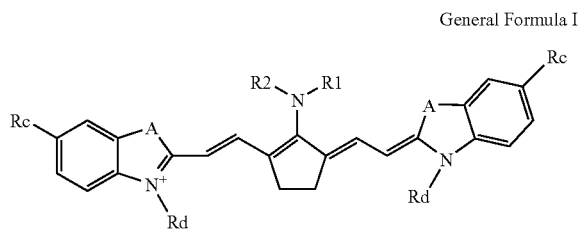

wherein:
R1 and R2 are substituted alkyl and may form a ring and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula II

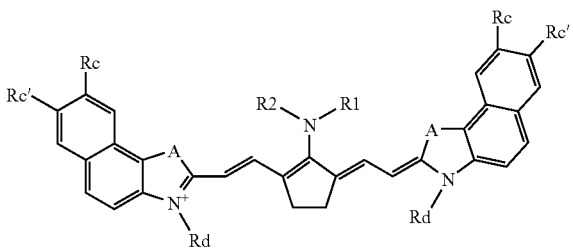

wherein:
R1 and R2 are substituted alkyl and are capable of forming a ring, and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula III

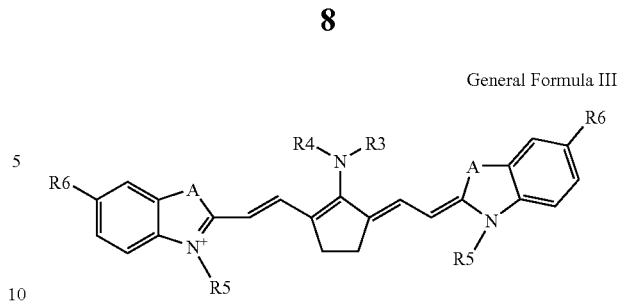

wherein:
A is NRa, S, O, Ra—C—Rb;
R3, R4, Ra, and Rb are substituted or unsubstituted alkyl capable of joining together to form a ring;
R6 is a SO3-;
R5 is substituted alkyl and at least one of the substituents is selected from a list of OH, NH2, COOH, maleimide, thiol, isocyante, isothiocyanate, disulfide, alkynyl, azidoyl, or trialkoxysilane;

General Formula IV

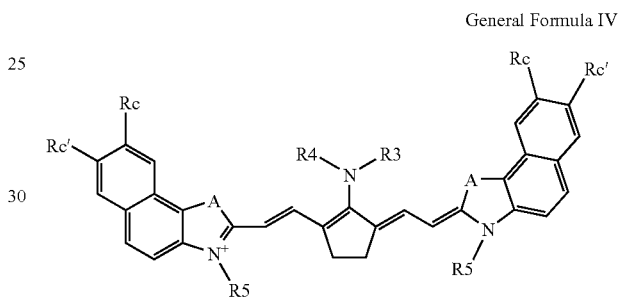

wherein:
A is NRa, S, O, Ra—C—Rb;
R3, R4, Ra, and Rb are substituted or unsubstituted alkyl capable of joining together to form a ring;
at least one of Rc and Rc' is a SO3-;
R5 is substituted alkyl and at least one of the substituents is selected from the group consisting of OH, NH2, COOH, maleimide, thiol, isocyante, isothiocyanate, disulfide, alkynyl, azidoyl, or trialkoxysilane;
Rc is hydrogen or SO3-, aryl, alkyl, alkoxy, or halogen; and General Formula V

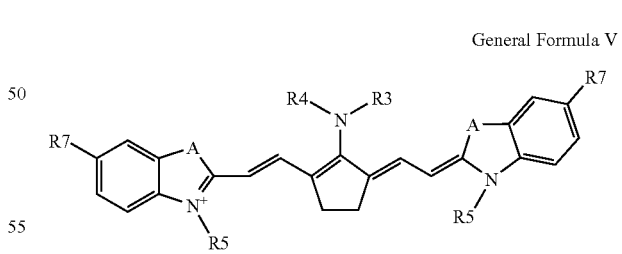

wherein:
A is NRa, S, O, Ra—C—Rb;
R3, R4, Ra, and Rb are substituted or unsubstituted alkyl capable of joining together to form a ring;
R7 is a COOH;
R5 is substituted alkyl and contains a SO3- group, and attaching a conjugate to said thereto a water dispersible, near-infrared tricarbocyanine, enamine-functionalized dye. The present invention also relates to a method of identifying a biological compound comprising providing at least one diagnostic contrast agent comprising at least one water dispersible, near-infrared tricarbocyanine, enamine-functionalized dye having a Stoke shift of greater than 50 and represented by the following five general formulae:

General Formula I

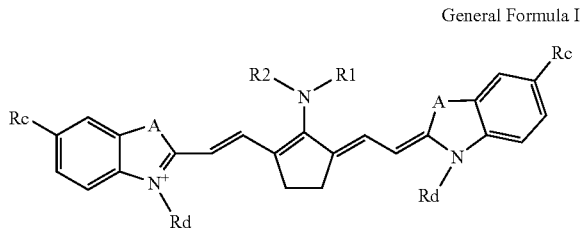

wherein:
R1 and R2 are substituted alkyl and may form a ring and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula II

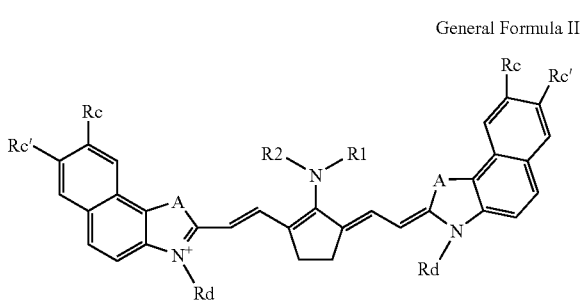

wherein
R1 and R2 are substituted alkyl and are capable of forming a ring, and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula III

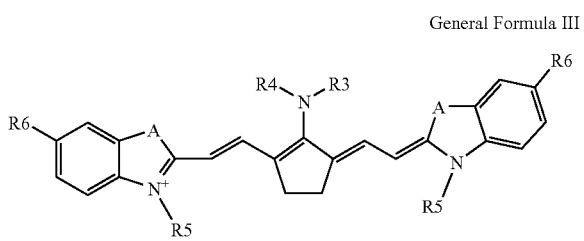

wherein:
A is NRa, S, O, Ra—C—Rb;
R3, R4, Ra, and Rb are substituted or unsubstituted alkyl capable of joining together to form a ring;
R6 is a SO3-;
R5 is substituted alkyl and at least one of the substituents is selected from a list of OH, NH2, COOH, maleimide, thiol, isocyante, isothiocyanate, disulfide, alkynyl, azidoyl, or trialkoxysilane;

General Formula IV

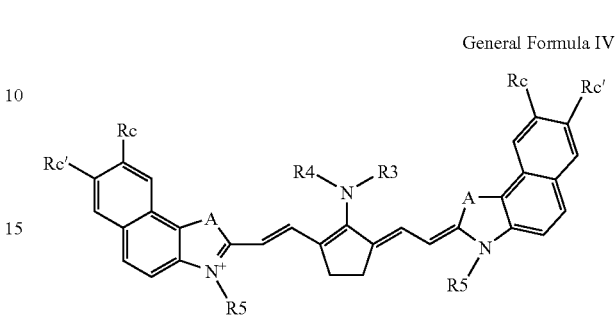

wherein:
A is NRa, S, O, Ra—C—Rb;
R3, R4, Ra, and Rb are substituted or unsubstituted alkyl capable of joining together to form a ring;
at least one of Rc and Rc' is a SO3-;
R5 is substituted alkyl and at least one of the substituents is selected from the group consisting of OH, NH2, COOH, maleimide, thiol, isocyante, isothiocyanate, disulfide, alkynyl, azidoyl, or trialkoxysilane;
Rc is hydrogen or SO3-, aryl, alkyl, alkoxy, or halogen; and General Formula V wherein:
A is NRa, S, O, Ra—C—Rb;
R3, R4, Ra, and Rb are substituted or unsubstituted alkyl capable of joining together to form a ring;
R7 is a COOH;
R5 is substituted alkyl and contains a SO3- group, and attaching a conjugate to a water dispersible, near-infrared tricarbocyanine, enamine-functionalized dye to form at least one water dispersible, near-infrared tricarbocyanine, enamine-functionalized dye-conjugate, wherein the conjugate is specific to a biological target material, adding the at least one water dispersible, near-infrared tricarbocyanine, enamine-functionalized dye-conjugate to an aqueous system containing at least one biological target material, illuminating the system with means for exciting fluorescence in the near-infrared tricarbocyanine, enamine-functionalized dye-conjugate, and visualizing the illuminated near-infrared tricarbocyanine, enamine-functionalized dye-conjugate.

ADVANTAGEOUS EFFECT OF THE INVENTION

The present invention includes several advantages, not all of which are incorporated in a single embodiment. The present invention provides a fluorescent dye for in-vitro and in-vivo imaging with an improved Stoke shift brightness. It is the object of this invention to provide a more simple method than complex chemical and optical coupling between multiple dyes and immobilizing multible dyes in a polymeric matrix to achieve an enhanced Stoke shift via the Förster resonance energy transfer mechanism. It is the object of this invention to provide dyes which by the very nature of their chemical structure exhibit inherently large Stoke shifts of substantially greater than 50 nm.

Fluorescent materials that incorporate bright fluorescent dyes with increased Stoke shift would permit maximum utilization of the available excitation and emission light, resulting in a greater fluorescence signal.

Another advantage of fluorescent materials with large Stoke shifts is that they can be more easily detected in the presence of other fluorescent materials.

A third advantage of fluorescent materials with large Stoke shifts is their usefulness in detecting multiple analytes in a single sample using a single excitation wavelength.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
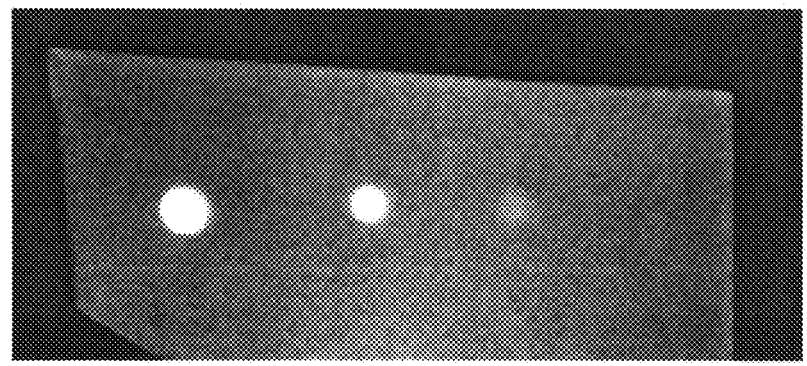
FIG. 1 illustrates the exposed nitrocellulose strip of experimental protein detected by tricarbocyanine-amine-functionalized dye labeled secondary antibody (Example 1).

The present invention relates to a water dispersible, near-infrared tricarbocyanine enamine-functionalized dye, which preferably exhibits polar solvatochromism due to a carboxyethylpiperazine (enamine) bridging group, and is represented by at least one of the following five formulas:

General Formula I

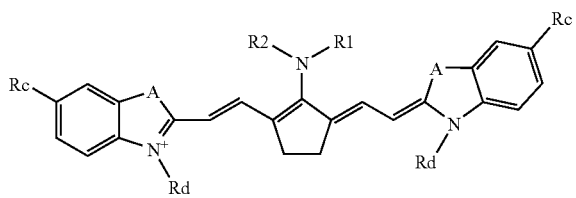

wherein:
R1 and R2 are substituted alkyl and may form a ring and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula II

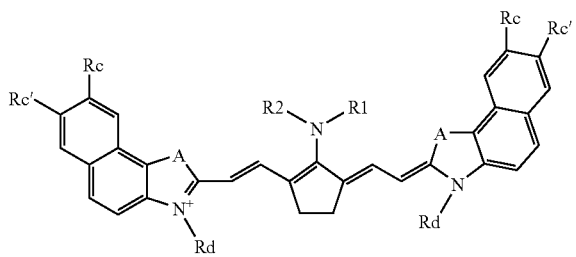

wherein:
R1 and R2 are substituted alkyl and are capable of forming a ring, and at least one of R1 or R2 is a linking group selected from a list of COOH, NH2, maleimide, thiol, isocyanate, isothiocyanate, disulfide, alkynyl, azidoyl, or trialkoxysilane;
A is NRa, S, O, Ra—C—Rb, wherein Ra and Rb are substituted or unsubstituted alkyl groups capable of forming a ring;
Rc is hydrogen or SO3-, aryl, alkyl, alkoxy, or halogen;
Rd is alkyl or (CH2)nSO3- where n=2 to 4, General Formula III

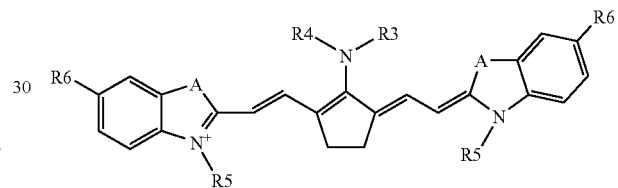

wherein:
A is NRa, S, O, Ra—C—Rb;
R3, R4, Ra, and Rb are substituted or unsubstituted alkyl capable of joining together to form a ring;
R6 is a SO3-;
R5 is substituted alkyl and at least one of the substituents is selected from a list of OH, NH2, COOH, maleimide, thiol, isocyante, isothiocyanate, disulfide, alkynyl, azidoyl, or trialkoxysilane;

General Formula IV

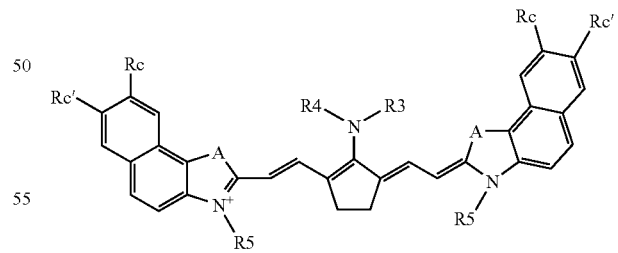

wherein:
A is NRa, S, O, Ra—C—Rb;
R3, R4, Ra, and Rb are substituted or unsubstituted alkyl capable of joining together to form a ring;
at least one of Rc and Rc' is a SO3-;
R5 is substituted alkyl and at least one of the substituents is selected from the group consisting of OH, NH2, COOH, maleimide, thiol, isocyante, isothiocyanate, disulfide, alkynyl, azidoyl, or trialkoxysilane;

Rc is hydrogen or SO3-, aryl, alkyl, alkoxy, or halogen;

General Formula V

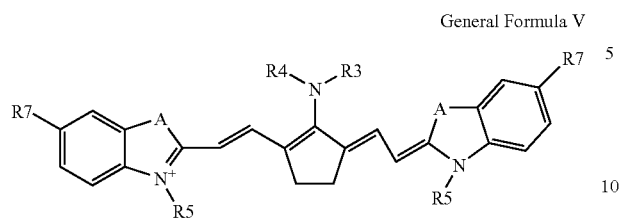

wherein:
A is NRa, S, O, Ra—C—Rb;
R3, R4, Ra, and Rb are substituted or unsubstituted alkyl capable of joining together to form a ring;
R7 is a COOH;
R5 is substituted alkyl and contains a SO3- group.
In a most preferred embodiment, Ra and Rb are methyl.
Preferred tricarbocyanine enamine-functionalized dye are:

Formula Ia

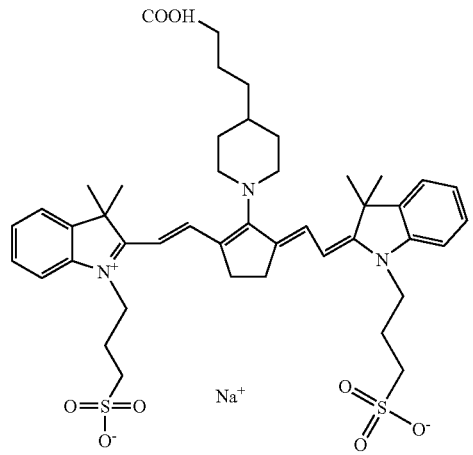

Other dyes of Formula I include:

Compound 6

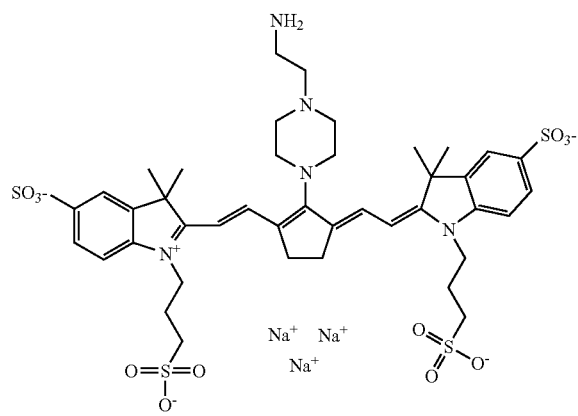

Compound 7

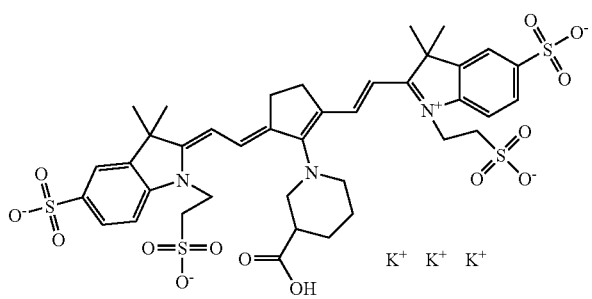

Compound 8

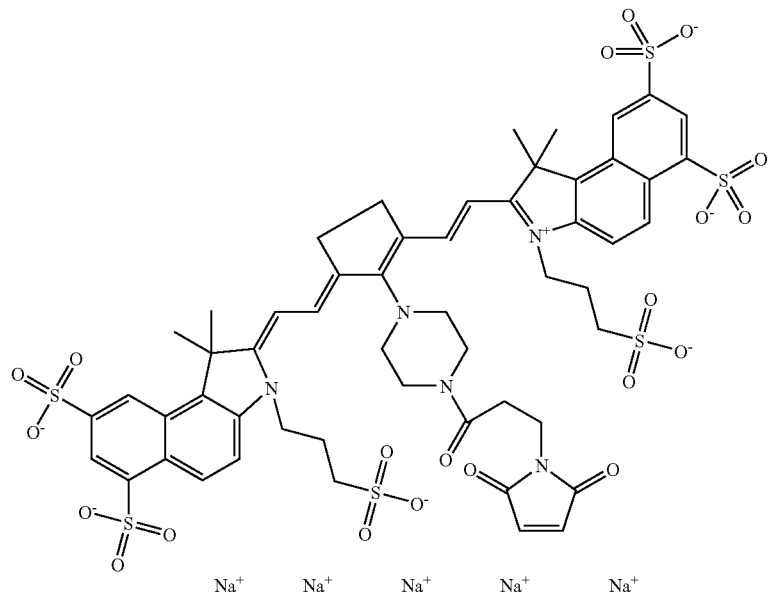

-continued
Compound 9
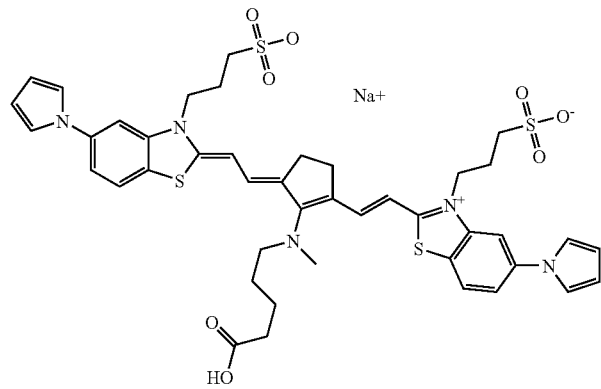
Compound 10
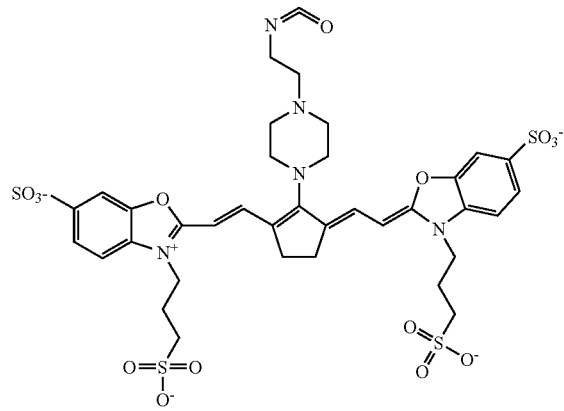
Compound 11
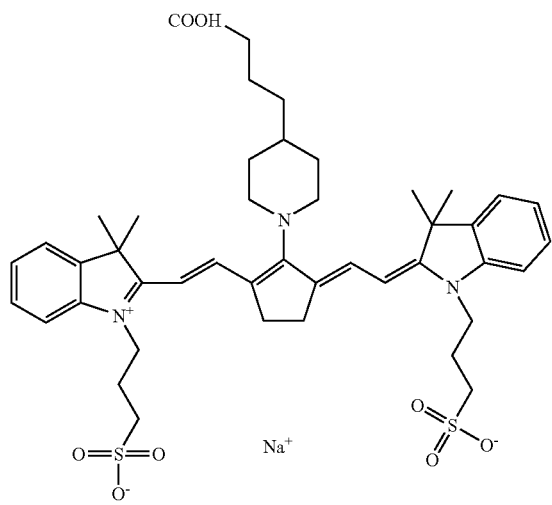
Compound 12
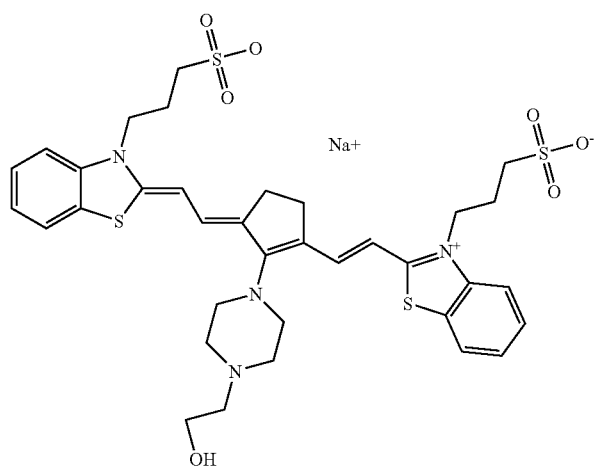
Compound 13
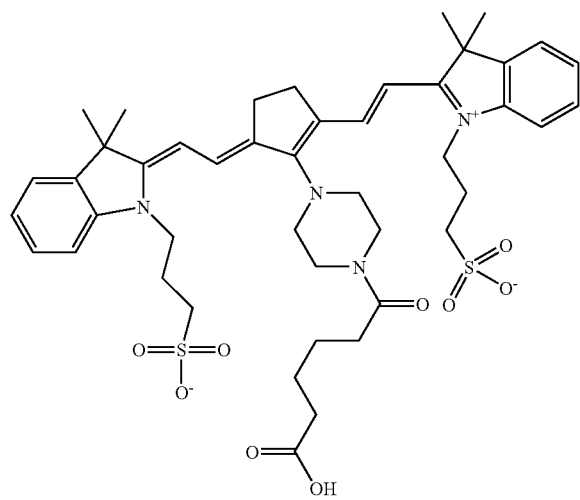
Compound 14
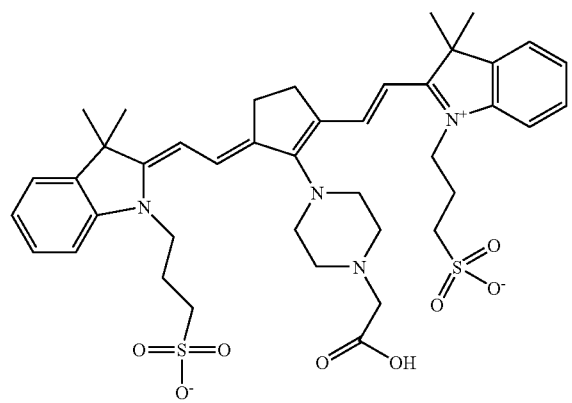

-continued
Compound 15
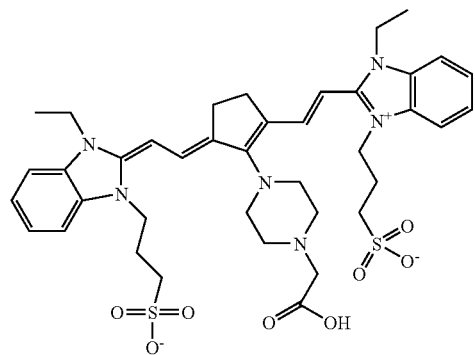
Compound 21
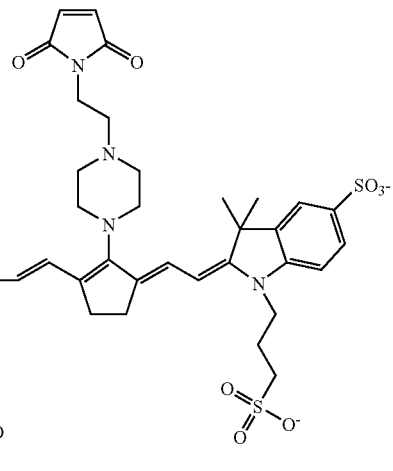
Compound 22
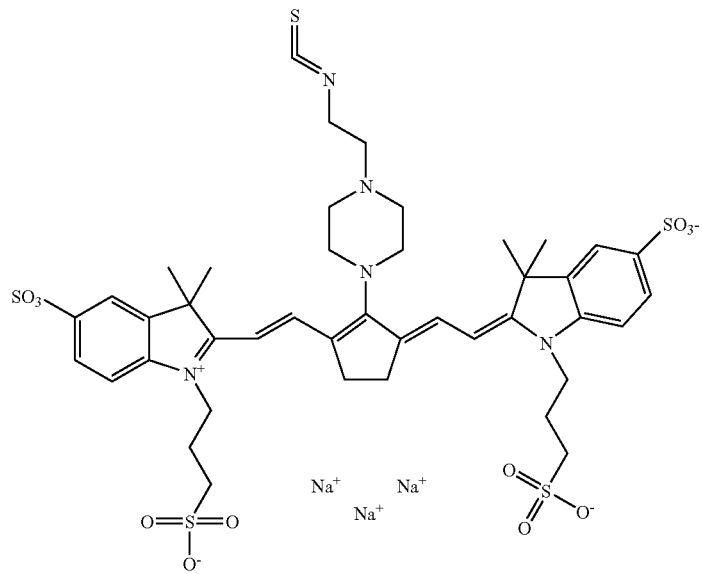
Formula IIa:
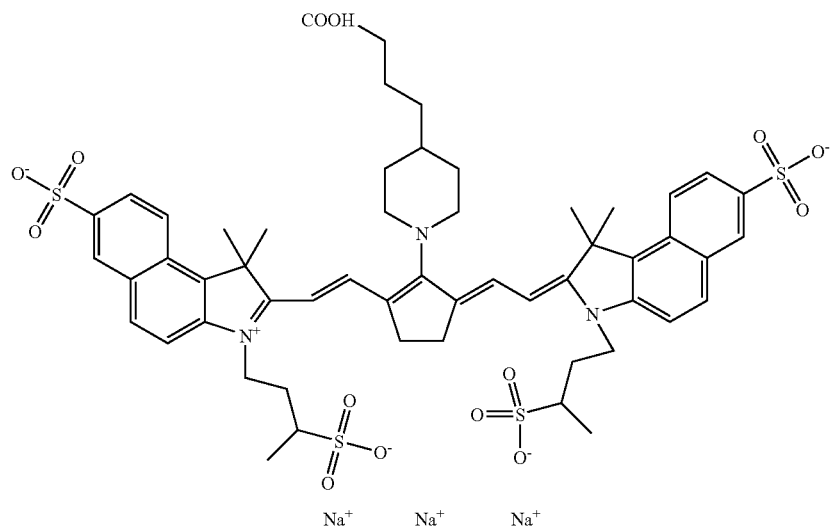

Other dyes of Formula II include:
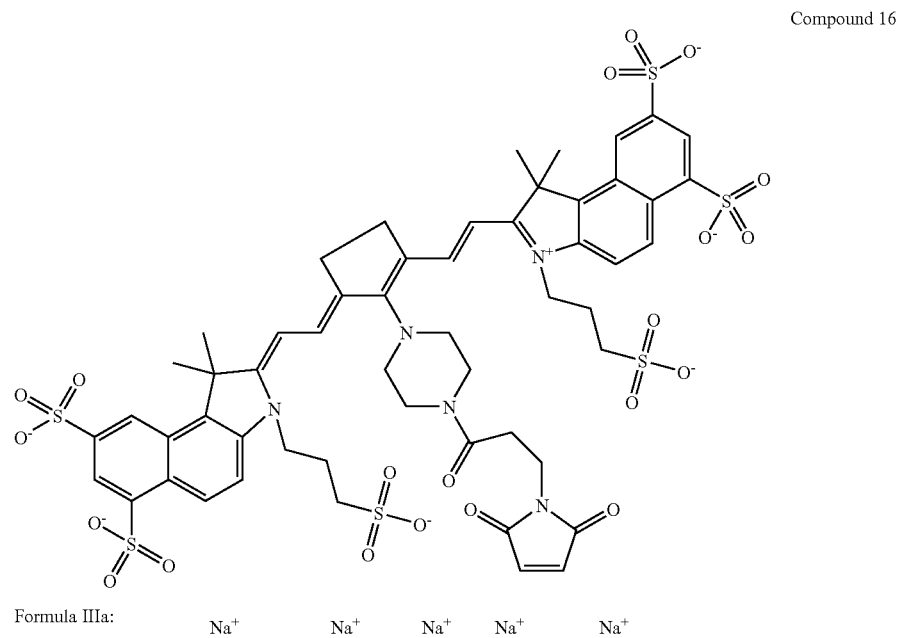
Compound 16
Formula IIIa:
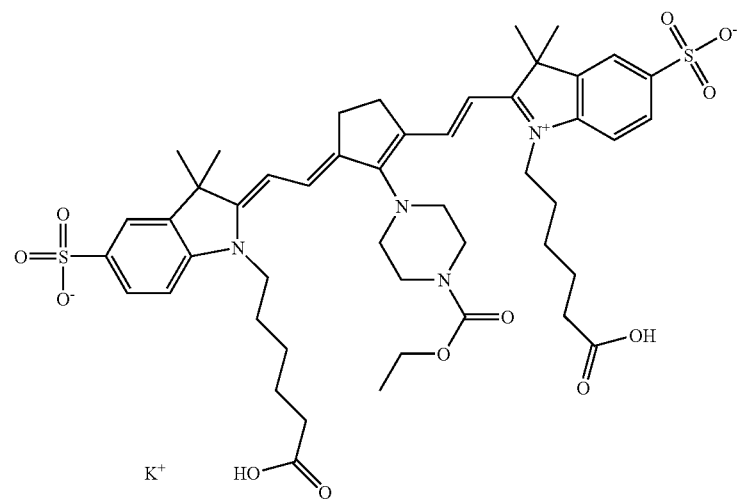
Other dyes of Formula III include:
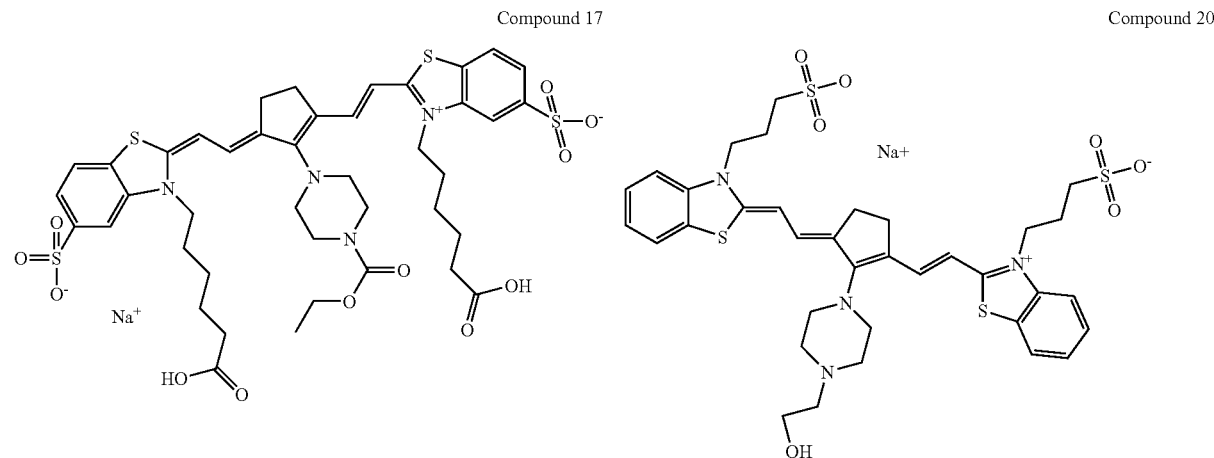
Compound 17
Compound 20

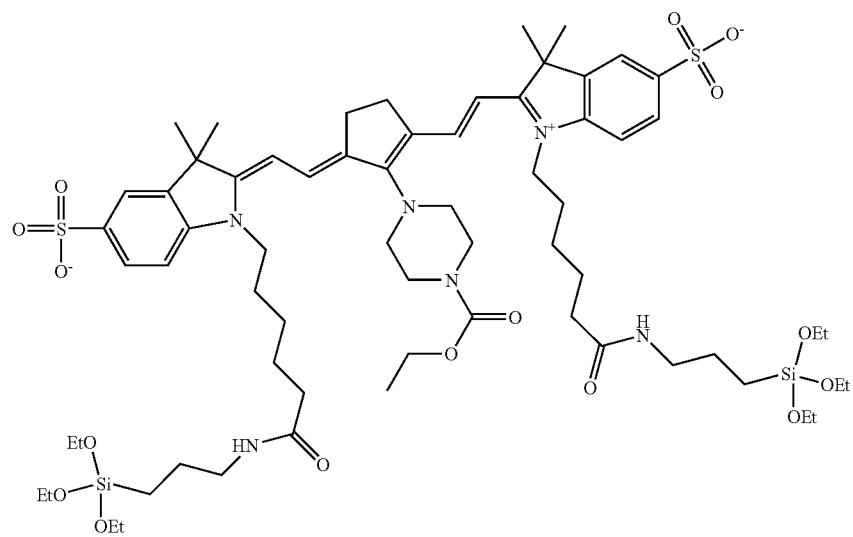
Compound 23
Formula IVa:
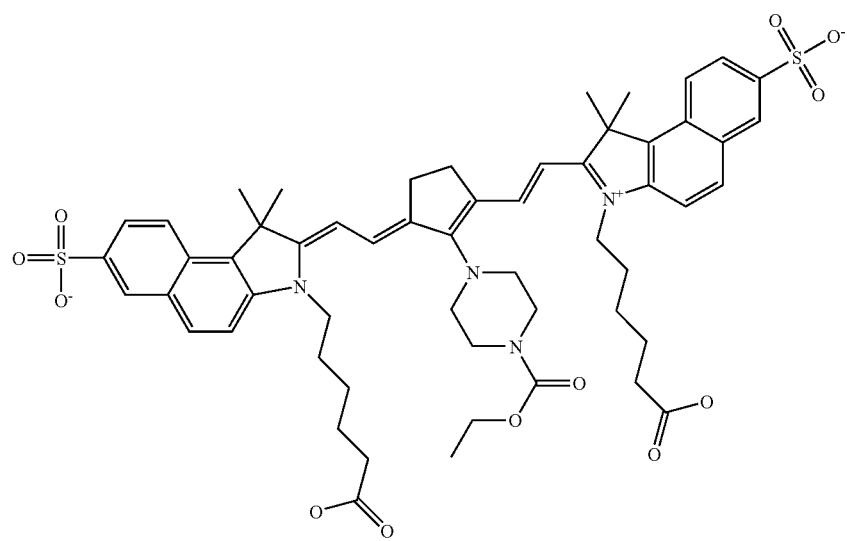

Other dyes of Formula IV include:
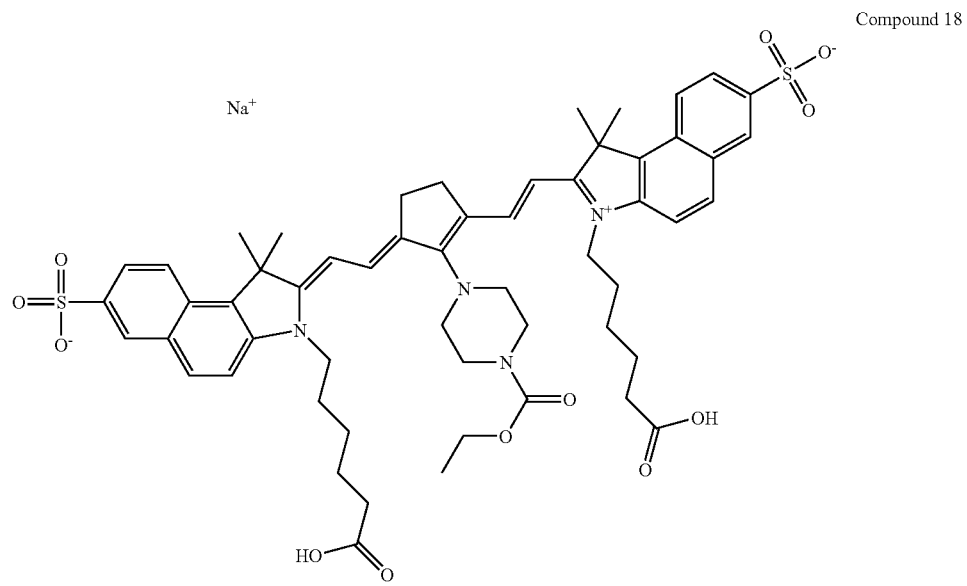
Compound 18
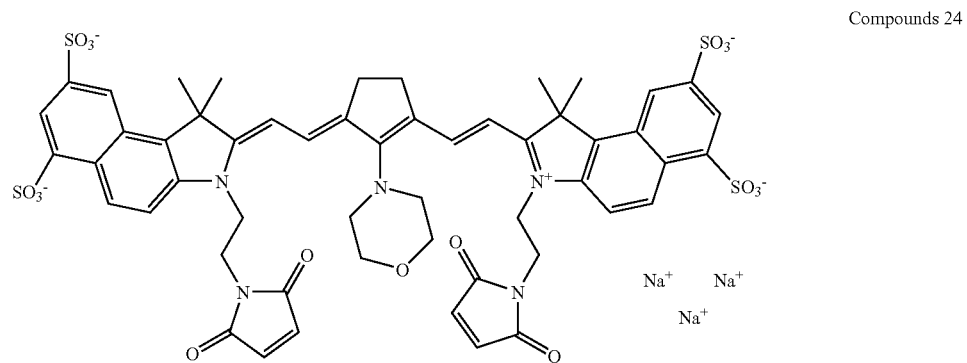
Compounds 24
Formula Va:
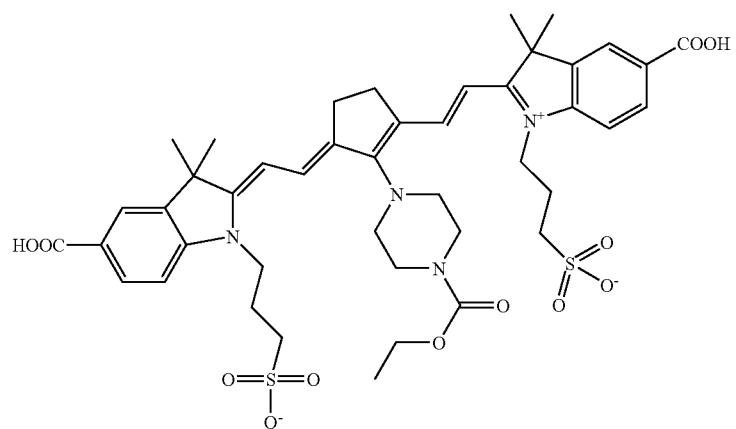

Other dyes of Formula V include:

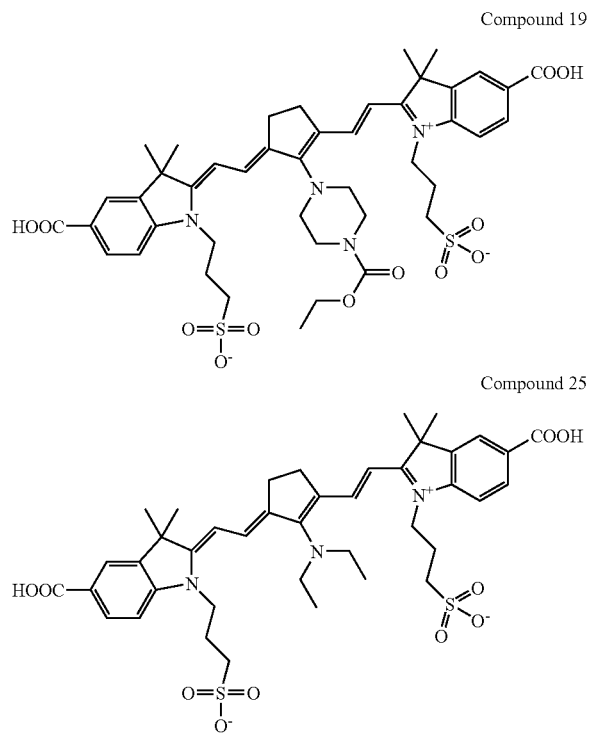

Compound 19

Compound 25

The enamine function of the tricarbocyanine, amine-functionalized dye is critical to the high Stoke shift. Other tricarbocyanineoxygen-functionalized or tricarbocyanine, sulfur-functionalized dye will exhibit high Stoke shifts.

Furthermore to ensure a large Stoke shift, the amine should be a dialkyl amine substituent on the ethylenic bridge. This dialkyl amine group should not be directly substituted with electron withdrawing substituents such as aryl groups or carbonyl group. The Comparative data shows a tricarbocyanine-sulfur-functionalized dyes as in Compound A, B, J, and K. The table shows tricarbocyanine- alkyl-functionalized dye, Compound E, and tricarbocyanine-chloro-functionalized dyes, Compound F and Compound I. The table also shows tricarbocyanine-amine functionalized dyes: Compounds C, D, G, and H in which the amines are not dialkyl amines and none of these examples have a large Stoke Shift greater than 50 nm. The present inventive compounds have a Stoke shift of at least 50 nm, preferably from 70-250, and most preferably from 70 to 140. Preferably, the water dispersible, near-infrared tricarbocyanine, enamine-functionalized dye has a max excitation wavelength between 500 and 900 nm, a maximum emission wavelength which is at least 70 nm greater in wavelength than the max excitation wavelength, or a combination thereof.

A good attachment group allows the dye to be covalently bonded to a biomolecule. The covalent attachment provides a link that is stable to handling, changes in solvent, pH, and ionic strength, and temperature. This stable association between the dye and the biomolecule is important to insure that the fluorescent signal that is detected relates to the presence of the biomolecule. If a dye is not covalently attached and associated with the biomolecule through ionic attraction, or Van der Waals forces then the dye may become detached and the desired biomolecule signal will decrease and false signals may be obtained from the dye alone. The attachment group should allow covalent bonding to occur in organic solvents such as N,N-dimethylformide, dimethylsulfoxide, N-methylpyrrolidone, and non organic solvents such as water.

The attachment group will allow the use of linkers that are designed to form covalent bonds between the attachment group on the dye and the attachment group on the biomolecule or other desired conjugate to allow for greater flexibility in the methods to for the desired attachment. Linkers may include, for example, hetero-bifunctional or homo-bifunctional linkers such as bis-sulfosuccinylsuberate, 3-[2-(aminoethyl)dithio]propionic acid, p-azidobenzoylhydrazide, bis-maleimidohexane, N-succinimidyl-S-acetylthioacetate, N-Sulfosuccinimidyl-4-azidophenyl-1-3'-dithiopropionatte, Succinimidyl 4-[p-maleimidophenyl]butyrate, N-Succinimidyl[4-iodoacetyl]aminobenzoate, Sulfosuccinimidyl-[perfluoroazidobenzamido]ethyl-1,3'-dithiopropionate, Succinimidyl 3-[bromoacetamido]propionate, Sulfosuccinimidyl 2-[7-amino-4-methylcoumarin-3-acetamido]ethyl-1, 3'dithiopropionate, β-(2-Pyridyldithio)propionyl hydrazide), N-e-Maleimidocaproyloxy]succinimide ester, N-[4-(p-Azidosalicylamido) butyl]-3'-(2'-pyridyldithio)propionamide, Succinimidyl 4-[N-maleimidomethyl]cyclohexane-1-carboxylate, 4-(4-N-Maleimidophenyl)butyric acid hydrazide hydrochloride, Disuccinimidyl suberate, Lomant's Reagent, Sulfosuccinimidyl[2-6-(biotinamido)-2-(p-azidobenzamido)-hexanoamido]-ethyl-1,3'-dithiopropionate, β-[Tris(hydroxymethyl)phosphino]propionic acid (betaine), (Sulfosuccinimidyl 4-[p-maleimidophenyl]butyrate), Bis-Maleimidoethane, Bis-[b-(4-Azidosalicylamido)ethyl] disulfide, Succinimidyl 4-[N-maleimidomethyl] cyclohexane-1-carboxy-[6-amidocaproate], N-[p-Maleimidophenyl]isocyanate, m-Maleimidobenzoyl-N-hydroxysulfosuccinimide ester, Sulfosuccinimidyl 4-N-maleimidomethyl cyclohexane-1-carboxylate, Bis [sulfosuccinimidyl] suberate, N-[g-Maleimidobutyryloxy] sulfosuccinimide ester, N-succinimidyl 4-pentynoate, and N-succinimidyl 4-azidoylbutanoate.

By the proper use of attachment groups, the dyes can be covalently attached to the biomolecule or other conjugate in such a way to optimize the fluorescent signal and not interfere with the normal function of the biomolecule or conjugate. The carboxylic acid attachment group can be converted to an active ester to enable the covalent bond formation. An N-hydroxysuccinimide ester is a preferred method of activating the carboxylic acid group. The carboxylic acid attachment group can also be activated for covalent bond formation with carbodiimide reagents such as dicylcohexylcarbodiimide. A hydroxyl attachment group can be activated for covalent bond formation by forming a chloroformate such as p-nitrophenyl chloroformate. An amine attachment group can be activated for covalent bond formation by forming using the carbodiimide activating agent to react with carboxylic acid functions of the biomolecule, or forming isocyanates or isothiocyanates or using an amine reactive linking group from the list above. The maleimide linking group can react with thiol groups typically available from cysteine residues in biomolecules or a thiol linking group from the list above, an isocyanate or isothiocyanate can be used directly to react with amine groups of a biomolecule. The trialkoxysilane can be use to react with other trialkoxysilanes or siloxide modified molecules or particles. The alkyne and azidoyl group can be used to form a stable triazole link often catalyzed by copper (I); such that if the dye contains an alkynyl attachment group, then an azidoyl attachment group is placed on the biomolecule or the opposite where an azidoyl group is the attachment group on the dye and an alkynyl group is added to the biomolecule.

IR-144 is a dye developed for use with lasers has the structure shown below. This dye does not meet the requirements of this invention because there is no suitable attachment group on the dye. Consequently, the dye cannot form covalent bonds with biomolecules or other conjugates utilized by the present invention and will not react with the list of linker groups shown above.

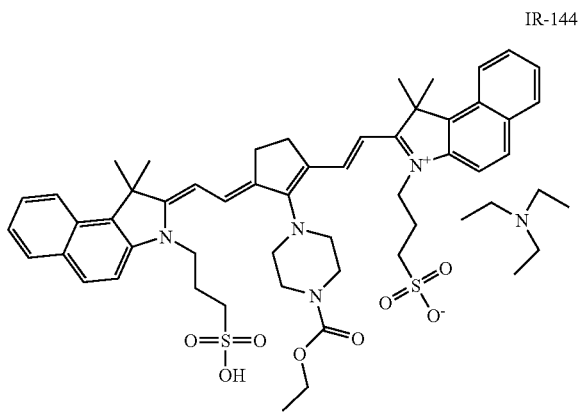

IR-144

The near-infrared tricarbocyanine, enamine-functionalized dyes contain reactive groups that will covalently attach to a conjugate, such as a target molecule or any other material to which the dye is desired to be attached, preferably at an amine or hydroxy site, and in some instances at a sulfhydryl site. In the present general formulas I and II, R1 and/or R2 preferably perform this function. In the present general formulas III-V, R3 and/or R4 preferably perform this function. In another most preferred embodiment, at least one of R1, R2, R3, R4 independently represents COOH.

Generally, any manner of forming a linkage between a biological, pharmaceutical or diagnostic component of interest and the near-infrared tricarbocyanine, enamine-functionalized dye can be utilized to form the attachment. This can include covalent, ionic, or hydrogen bonding of the ligand to the exogenous molecule, either directly or indirectly via a linking group. The linkage is typically formed by covalent bonding of the biological, pharmaceutical or diagnostic component to the dye through the formation of amide, ester or imino bonds between acid, aldehyde, hydroxy, amino, or hydrazo groups on the respective components of the complex. Art-recognized biologically labile covalent linkages such as imino bonds isocyanates, isothiocyanates, alkynyl, azidoyl, trialkoxysilanend so-called "active" esters having the linkage —COON—, - or —COOAr are preferred. Hydrogen bonding, e.g., that occurring between complementary strands of nucleic acids, can also be used for linkage formation.

The characteristically large Stoke shift exhibited by the water dispersible, near-infrared tricarbocyanine, enamine-functionalized dyes may prove useful for fluorescence optical molecular imaging applications. In a preferred embodiment, the dye is associated with another component to form a dye-conjugate. Preferably, the other component is a biological component. Near-infrared tricarbocyanine, enamine-functionalized dyes can also be used to label non-biological materials, such as soluble polymers and polymeric particles, glass, monomers, drugs and other surfaces and particles which contain or are derivatized to contain functionalities capable of binding covalently to the amino, hydroxy or sulfhydryl reactive nucleophiles of the cyanine dye molecule.

The component being labeled can be in a mixture including other materials. The mixture, in which the labeling reaction occurs, can be a liquid mixture, particularly a water mixture. The detection step can occur with the mixture in a liquid or dry condition, such as a microscope slide.

"Labeling" refers to the attachment of the dye or dye conjugate to a material to aid in the identification of the material. Preferably, the material is identified by optical detection methods.

"Biocompatible" means that a composition does not disrupt the normal function of the bio-system into which it is introduced. Typically, a biocompatible composition will be compatible with blood and does not otherwise cause an adverse reaction in the body. For example, to be biocompatible, the material should not be toxic, immunogenic or thrombogenic.

"Biodegradable" means that the material can be degraded either enzymatically or hydrolytically under physiological conditions to smaller molecules that can be eliminated from the body through normal processes.

The term "diagnostic agent" includes components that can act as contrast agents and thereby produce a detectable indicating signal in the host or test sample. The detectable indicating signal may be gamma-emitting, radioactive, echogenic, fluoroscopic or physiological signals, or the like.

The term "biomedical agent" as used herein includes biologically active substances which are effective in the treatment of a physiological disorder, pharmaceuticals, enzymes, hormones, steroids, recombinant products and the like. Exemplary therapeutic agents are antibiotics, thrombolytic enzymes such as urokinase or streptokinase, insulin, growth hormone, chemotherapeutics such as adriamycin and antiviral agents such as interferon and acyclovir.

In one preferred embodiment, the dye is associated with a material that is selective for a target material to be labeled and optionally detected. For example, nucleic acid detection generally involves probing a sample thought to contain target nucleic acids using a nucleic acid probe that contains a nucleic acid sequence that specifically recognizes the sequence of the target nucleic acids, such that the nucleic acid probe and the target nucleic acids in combination create a hybridization pair. The nucleic acid probe typically contains from greater than about 4 bases to as many as tens of thousands of bases, although probing entire chromosomes may involve millions of bases. Any of the dye-conjugates described below may be used to label the corresponding target materials.

The component or conjugate to which the dye is attached, also referred to as the labeled component, can be antibodies, proteins, peptides, enzyme substrates, hormones, lymphokines, metabolites, receptors, antigens, haptens, lectins, toxins, carbohydrates, sugars, oligosaccharides, polysaccharides, nucleic acids, deoxy nucleic acids, derivatized nucleic acids, derivatized deoxy nucleic acids, DNA fragments, RNA fragments, derivatized DNA fragments, derivatized RNA fragments, natural drugs, virus particles, bacterial particles, virus components, yeast components, blood cells, blood cell components, biological cells, noncellular blood components, bacteria, bacterial components, natural and synthetic lipid vesicles, synthetic drugs, poisons, environmental pollutants, polymers, polymer particles, glass particles, glass surfaces, plastic particles and plastic surfaces.

A variety of dye-conjugates may be prepared using the reactive dyes of the invention, including conjugates of antigens, steroids, vitamins, drugs, haptens, metabolites, toxins, environmental pollutants, amino acids, peptides, proteins, nucleic acids, nucleic acid polymers, carbohydrates, lipids, and polymers. In another embodiment, the conjugated substance is an amino acid, peptide, protein, polysaccharide, nucleotide, oligonucleotide, nucleic acid, hapten, drug, lipid, phospholipid, lipoprotein, lipopolysaccharide, liposome, lipophilic polymer, polymer, polymeric microparticle, biological cell or virus. In one aspect of the invention, the conjugated substance is labeled with a plurality of dyes of the present invention, which may be the same or different.

The near-infrared tricarbocyanine, enamine-functionalized dyes are useful as labels for probes and in immunoassays and also as labels for in-vivo imaging and in-vivo tumor therapy. When so used, these dye components may be linked to one member of a specific binding pair ("labeled binding partner") or an analog of such a member to form a dye-conjugate.

These dyes may be used as agents for in-vivo imaging. When used as imaging agents, these dyes are conjugated to one member of a specific binding pair to give a labeled conjugate/binding complement. The dye-conjugate is introduced into an animal. If the other member of the specific binding pair is present, the dye-conjugate will bind thereto and the signal produced by the dye may be measured and its localization identified.

These dyes may also be used in in-vivo tumor therapy. For example, photodynamic therapy involves using the dye component as a photosensitizing agent. The dye is conjugated to a binding partner which may specifically recognize and bind to a component of a tumor cell. The localized triplet emission from the bound dye-conjugate after excitation by light, causes chemical reactions and selective damage and/or destruction to the tumor cells.

The near-infrared tricarbocyanine, enamine-functionalized dye or dye-conjugate may also be utilized with biocompatible beads, microbeads or nanoparticles. The components can be associated with the dye through a linkage. By "associated with", it is meant that the dye or dye-conjugate is carried by the nanoparticle, for example the shell of a core-shell nanoparticle. The dye or dye-conjugate can be dissolved and incorporated in the particle non-covalently. A preferred method of associating the dye or dye-conjugate is by covalent bonding through an amine function on the outside of a particle.

In a preferred embodiment, the dyes are covalently attached to the surface of the beads. This may be done as is generally outlined for the attachment of the bioactive agents, using functional groups on the surface of the beads.

In a preferred embodiment, the dyes are non-covalently associated with the beads, generally by entrapping the dyes in the bead matrix or pores of the beads.

In a preferred embodiment, the dyes or dye-conjugates are used to probe a sample solution for the presence or absence of a target analyte. By "target analyte" or "analyte" or grammatical equivalents herein is meant any atom, molecule, ion, molecular ion, compound or particle to be either detected or evaluated for binding partners. As will be appreciated by those in the art, a large number of analytes may be used in the present invention; basically, any target analyte can be used which binds a bioactive agent or for which a binding partner (i.e. drug candidate) is sought.

The target material is optionally a material of biological or synthetic origin that is present as a molecule or as a group of molecules, including, but not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids), DNA and RNA fragments and derivatized fragments (including single and multi-stranded fragments), natural and synthetic drugs, receptors, virus particles, bacterial particles, virus components, biological cells, spores, cellular components (including cellular membranes and organelles), natural and synthetic lipid vesicles, polymer membranes, polymer surfaces and particles, and glass and plastic surfaces and particles. Typically the target material is present as a component or contaminant of a sample taken from a biological or environmental system. Particularly preferred analytes are nucleic acids and proteins.

In one aspect of the invention, the conjugate is a bioreactive substance. The target material is optionally a bioreactive substance also. Bioreactive substances are substances that react with or bind to molecules that are derived from a biological system, whether such molecules are naturally occurring or result from some external disturbance of the system (e.g. disease, poisoning, genetic manipulation). By way of illustration, bioreactive substances include biomolecules (i.e. molecules of biological origin including, without limitation, polymeric biomolecules such as peptides, proteins, polysaccharides, oligonucleotides, avidin, streptavidin, DNA and RNA, as well as non-polymeric biomolecules such as biotin and digoxigenin and other haptens typically having a MW less than 1000), microscopic organisms such as viruses and bacteria, and synthetic haptens (such as hormones, vitamins, or drugs). Typically the target complement or the target material or both are amino acids, peptides (including polypeptides), or proteins (larger MW than polypeptides); or are nucleotides, oligonucleotides (less than 20 bases), or nucleic acids (i.e. polymers larger than oligonucleotides, including RNA and single- and multi-stranded DNA and fragments and derivitized fragments thereof); or are carbohydrates or carbohydrate derivatives, including monosaccharides, polysaccharides, oligosaccharides, glycolipids, and glycoproteins; or are haptens (a chemical compound that is unable to elicit an immunological response unless conjugated to a larger carrier molecule), which haptens are optionally conjugated to other biomolecules; or a microscopic organisms or components of microscopic organisms. For such bioreactive substances, there are a variety of known methods for selecting useful pairs of corresponding conjugates complementary to the target materials.

Where more than one material is targeted simultaneously, multiple conjugates which are target complements (one for each corresponding target material) are optionally included. Target complements are selected to have the desired degree of specificity or selectivity for the intended target materials.

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins. In a preferred embodiment, the target analyte is a nucleic acid. In a preferred embodiment, the probes are used in genetic diagnosis. For example, probes can be made using the techniques disclosed herein to detect target sequences such as the gene for nonpolyposis colon cancer, the BRCA1 breast cancer gene, P53, which is a gene associated with a variety of cancers, the Apo E4 gene that indicates a greater risk of Alzheimer's disease, allowing for easy presymptomatic screening of patients, mutations in the cystic fibrosis gene, or any of the others well known in the art.

In an additional embodiment, viral and bacterial detection is done using the complexes of the invention. In this embodiment, probes are designed to detect target sequences from a variety of bacteria and viruses. For example, current blood-screening techniques rely on the detection of anti-HIV antibodies. The methods disclosed herein allow for direct screening of clinical samples to detect HIV nucleic acid sequences, particularly highly conserved HIV sequences. In addition, this allows direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected.

In a preferred embodiment, the nucleic acids of the invention find use as probes for toxic bacteria in the screening of water and food samples. For example, samples may be treated to lyse the bacteria to release its nucleic acid, and then probes designed to recognize bacterial strains, including, but not limited to, such pathogenic strains as, *Salmonella, Campylobacter, Vibrio cholerae, Leishmania*, enterotoxic strains of *E. coli*, and Legionnaire's disease bacteria.

The described composition can further comprise a biological, pharmaceutical or diagnostic component that includes a targeting moiety that recognizes a specific target cell. Recognition and binding of a cell surface receptor through a targeting moiety associated with near-infrared tricarbocyanine, enamine-functionalized dyes can be a feature of the described compositions. This feature takes advantage of the understanding that a cell surface binding event is often the initiating step in a cellular cascade leading to a range of events, notably receptor-mediated endocytosis. The term "receptor mediated endocytosis" ("RME") generally describes a mechanism by which, catalyzed by the binding of a ligand to a receptor disposed on the surface of a cell, a receptor-bound ligand is internalized within a cell. Many proteins and other structures enter cells via receptor mediated endocytosis, including insulin, epidermal growth factor, growth hormone, thyroid stimulating hormone, nerve growth factor, calcitonin, glucagon and many others.

Receptor Mediated Endocytosis (hereinafter "RME") affords a convenient mechanism for transporting a dye-conjugate, possibly in combination with other biological, pharmaceutical or diagnostic components, to the interior of a cell.

In RME, the binding of a ligand by a receptor disposed on the surface of a cell can initiate an intracellular signal, which can include an endocytosis response. Thus, a near-infrared tricarbocyanine, enamine-functionalized dye with a targeting moiety associated to form a dye-conjugate, can bind on the surface of a cell and subsequently be invaginated and internalized within the cell. A representative, but non-limiting, list of moieties that can be employed as targeting agents useful with the present compositions is selected from the group consisting of proteins, peptides, aptomers, small organic molecules, toxins, diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, epidermal growth factor, growth hormone, thyroid stimulating hormone, nerve growth factor, calcitonin, glucagon, prolactin, luteinizing hormone, thyroid hormone, platelet derived growth factor, interferon, catecholamines, peptidomimetrics, glycolipids, glycoproteins and polysaccharides. Homologs or fragments of the presented moieties can also be employed. These targeting moieties can be associated with a near-infrared tricarbocyanine, enamine-functionalized dye and be used to direct the dye-conjugate to a target cell, where it can subsequently be internalized. There is no requirement that the entire moiety be used as a targeting moiety. Smaller fragments of these moieties known to interact with a specific receptor or other structure can also be used as a targeting moiety.

An antibody or an antibody fragment represents a class of most universally used targeting moiety that can be utilized to enhance the uptake of dye or dye-conjugate into a cell. Antibodies may be prepared by any of a variety of techniques known to those of ordinary skill in the art. See, e.g., Harlow and Lane, Antibodies: A Laboratory Manual, Cold Spring Harbor Laboratory, 1988. Antibodies can be produced by cell culture techniques, including the generation of monoclonal antibodies or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). A superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, Eur. J. Immunol, 6:511-519, 1976, and improvements thereto.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides may be used in the purification process in, for example, an affinity chromatography step.

A number of "humanized" antibody molecules comprising an antigen-binding site derived from a non-human immunoglobulin have been described (Winter et al. (1991) Nature 349:293-299; Lobuglio et al. (1989) Proc. Nat. Acad. Sci. USA 86:4220-4224. These "humanized" molecules are designed to minimize unwanted immunological response toward rodent antihuman antibody molecules that limits the duration and effectiveness of therapeutic applications of those moieties in human recipients.

Vitamins and other essential minerals and nutrients can be utilized as targeting moiety to enhance the uptake of near-infrared tricarbocyanine, enamine-functionalized dye or dye-conjugate by a cell. In particular, a vitamin ligand can be selected from the group consisting of folate, folate receptor-binding analogs of folate, and other folate receptor-binding ligands, biotin, biotin receptor-binding analogs of biotin and other biotin receptor-binding ligands, riboflavin, riboflavin receptor-binding analogs of riboflavin and other riboflavin receptor-binding ligands, and thiamin, thiamin receptor-binding analogs of thiamin and other thiamin receptor-binding ligands. Additional nutrients believed to trigger receptor mediated endocytosis, and thus also having application in accordance with the presently disclosed method, are carnitine, inositol, lipoic acid, niacin, pantothenic acid, pyridoxal, and ascorbic acid, and the lipid soluble vitamins A, D, E and K. Furthermore, any of the "immunoliposomes" (liposomes having an antibody linked to the surface of the liposome) described in the prior art are suitable for use with the described dyes or dye conjugates.

Since not all natural cell membranes possess biologically active biotin or folate receptors, use of the described compositions in-vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

RME is not the exclusive method by which the near-infrared tricarbocyanine, enamine-functionalized dyes or dye-conjugates can be translocated into a cell. Other methods of uptake that can be exploited by attaching the appropriate entity to a near-infrared tricarbocyanine, enamine-functionalized dye or dye-conjugate include the advantageous use of membrane pores. Phagocytotic and pinocytotic mechanisms also offer advantageous mechanisms by which a near-infrared tricarbocyanine, enamine-functionalized dye or dye-conjugate can be internalized inside a cell.

The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

The water dispersible, near-infrared tricarbocyanine, enamine-functionalized dye may also be useful in other biomedical applications, including, but not limited to, tomographic imaging of organs, monitoring of organ functions, coronary angiography, fluorescence endoscopy, detection, imaging, determining efficacy of drug delivery, and therapy of tumors, laser assisted guided surgery, photoacoustic methods, and sonofluorescent methods.

The compositions of the invention can be formulated into diagnostic compositions for enteral or parenteral administration. These compositions contain an effective amount of the dye along with conventional pharmaceutical carriers and excipients appropriate for the type of administration contemplated. For example, parenteral formulations advantageously contain a sterile aqueous solution or suspension of dye according to this invention. Parenteral compositions may be injected directly or mixed with a large volume parenteral composition for systemic administration. Such solutions also may contain pharmaceutically acceptable buffers and, optionally, electrolytes such as sodium chloride.

Formulations for enteral administration may vary widely, as is well known in the art. In general, such formulations are liquids which include an effective amount of the dye in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement. Such doses may vary widely, depending upon the particular dye employed, the organs or tissues which are the subject of the imaging procedure, the imaging equipment being used, and the like.

The diagnostic compositions of the invention are used in the conventional manner. The compositions may be administered to a patient, typically a warm-blooded animal, either systemically or locally to the organ or tissue to be imaged, and the patient then subjected to the imaging procedure.

Preferred administration techniques include parenteral administration, intravenous administration and infusion directly into any desired target tissue, including but not limited to a solid tumor or other neoplastic tissue. Purification can be achieved by employing a final purification step, which disposes the nanoparticle composition in a medium comprising a suitable pharmaceutical composition. Suitable pharmaceutical compositions generally comprise an amount of the desired nanoparticle with active agent in accordance with the dosage information (which is determined on a case-by-case basis). The described particles are admixed with an acceptable pharmaceutical diluent or excipient, such as a sterile aqueous solution, to give an appropriate final concentration. Such formulations can typically include buffers such as phosphate buffered saline (PBS), or additional additives such as pharmaceutical excipients, stabilizing agents such as BSA or HSA, or salts such as sodium chloride.

For parenteral administration it is generally desirable to further render such compositions pharmaceutically acceptable by insuring their sterility, non-immunogenicity and non-pyrogenicity. Such techniques are generally well known in the art. Moreover, for human administration, preparations should meet sterility, pyrogenicity, general safety and purity standards as required by FDA Office of Biological Standards. When the described nanoparticle composition is being introduced into cells suspended in a cell culture, it is sufficient to incubate the cells together with the nanoparticle in an appropriate growth media, for example Luria broth (LB) or a suitable cell culture medium. Although other introduction methods are possible, these introduction treatments are preferable and can be performed without regard for the entities present on the surface of a nanoparticle carrier.

The dye-conjugates described above, whether for single or multicolor detection systems, are combined with a sample thought to contain target materials. Typically the sample is incubated with an aqueous suspension of the near-infrared tricarbocyanine, enamine-functionalized dye-conjugates. Where a single color detection system is used, the aqueous suspension contains substantially identical near-infrared tricarbocyanine, enamine-functionalized dye-conjugates. Where a multicolor detection system is used, the aqueous suspension contains a number of detectably different near-infrared tricarbocyanine, enamine-functionalized dye-conjugates. In each case, the near-infrared tricarbocyanine, enamine-functionalized dye-conjugates is specific for a particular target or combination of targets.

Prior to combination with the near-infrared tricarbocyanine, enamine-functionalized dye-conjugates, the sample is prepared in a way that makes the target materials in the sample accessible to the probes. The target materials may require purification or separation prior to labeling or detection. For example, the sample may contain purified nucleic acids, proteins, or carbohydrates, either in mixtures or individual nucleic acid, protein, or carbohydrate species; the sample may contain nucleic acids, proteins, or carbohydrates in lysed cells along with other cellular components; or the sample may contain nucleic acids, proteins, or carbohydrates in substantially whole, permeabilized cells. Preparation of the sample will depend on the way the target materials are contained in the sample. When the sample contains cellular nucleic acids (such as chromosomal or plasmid borne genes within cells, RNA or DNA viruses or mycoplasma infecting cells, or intracellular RNA) or proteins, preparation of the sample involves lysing or permeabilizing the cell, in addition to the denaturation and neutralization already described.

Following the labeling of the sample with the near-infrared tricarbocyanine, enamine-functionalized dye-conjugates, unbound near-infrared tricarbocyanine, enamine-functionalized dye-conjugates are optionally removed from the sample by conventional methods such as washing.

For detection of the target materials, the sample is illuminated with means for exciting fluorescence in the near-infrared tricarbocyanine, enamine-functionalized dye-conjugates. Typically a source of excitation energy emitting within the range of the excitation peak of the near-infrared tricarbocyanine, enamine-functionalized dye-conjugates is used. Fluorescence resulting from the illuminated near-infrared tricarbocyanine, enamine-functionalized dye-conjugates that have formed a complex with the target materials can be used to detect the presence, location, or quantity of target materials.

Fluorescence from the near-infrared tricarbocyanine, enamine-functionalized dye-conjugates can be visualized with a variety of imaging techniques, including ordinary light or fluorescence microscopy and laser scanning confocal microscopy. Three-dimensional imaging resolution techniques in confocal microscopy utilize knowledge of the microscope's point spread function (image of a point source) to place out-of-focus light in its proper perspective. Multiple labeled target materials are optionally resolved spatially, chronologically, by size, or using detectably different spectral characteristics (including excitation and emission maxima, fluorescence intensity, or combinations thereof). Typically, multiple labeled target materials are resolved using different near-infrared tricarbocyanine, enamine-functionalized dye-conjugates with distinct spectral characteristics for each target material. Alternatively, the near-infrared tricarbocyanine, enamine-functionalized dye-conjugates are the same but the samples are labeled and viewed sequentially or spatially separated. If there is no need or desire to resolve multiple targets, as in wide scale screening (e.g. pan-viral or bacterial contamination screening), near-infrared tricarbocyanine, enamine-functionalized dye-conjugates containing multiple target complements need not be separately applied to samples.

The following examples are provided to illustrate the invention.

Example 1

Tricarbocyanine-Amine Functionalized Dye Labeled Antibody for Protein Assay

Conversion of Dye into N-Hydroxysuccinimide (NHS) Ester

To a solution of Compound 1 (120 mg) in dimethylformamide (DMF) (8 ml) was added N,N-disuccinimidyl carbonate (0.2 g), the resulting mixture was heated at 10° C. for half hour. The mixture was cooled to room temperature, ether was added, the solid product G (122 mg) was obtained. The product was pure based on its HPLC.

Covalent Attachment of Compound 1 to a Secondary Antibody

The dye N-hydroxysuccinimide (NHS) ester (0.05 mg) was added to a mixture of 0.5 mg of goat anti-rabbit secondary antibody in 200 ul of 0.15 molar phosphate buffered saline (PBS) and stirred for one hour at room temperature. The product was purified by size exclusion chromatography to yield the desired dye covalently bound to the antibody.

Protein Assay

A small piece of nitrocellulose was spotted with target rabbit protein and allowed to stand for 15 minutes. The prepared slide was treated with 5% blotto in PBS solution for 30 minutes and washed with fresh PBS solution.

A solution of the dye labeled antibody in 5% nonfat powdered milk (blotto) dissolved in PBS was rocked with the test nitrocellulose for 30 minutes and then washed with fresh PBS. The nitrocellulose strip was placed in a Kodak Image Station MM4000 (cooled CCD imaging with multiwavelength fluorescent illumination) and exposed for 1 minute to record fluorescence. As shown in FIG. 1, the bright spots on the nitrocellulose strip indicate the labeled secondary antibody binding to very low levels of spotted rabbit protein.

The dye labeled antibody was measured in a fluorimeter and the maximum excitation was at 637 nm and the maximum emission was at 773 nm for a Stoke shift of 136 nm for the labeled material.

Example 2

Figure 2:
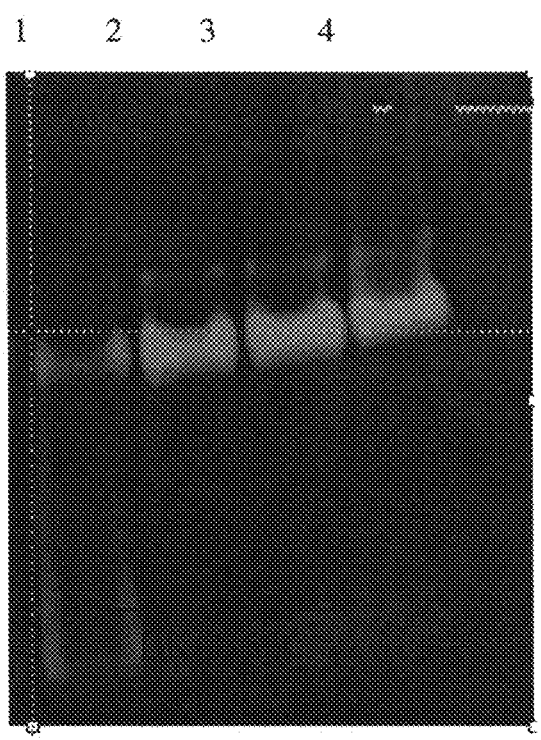
FIG. 2 illustrates the exposed polyacylamide gel plate of biotin labeled Bombesin peptide detected by a tricarbocyanine-amine-labeled dye labeled avidin.

Tricarbocyanine-Amine-Functionalized Dye Labeled Avidin for Detection of Biotin Labeled Protein In another example, the N-hydroxysuccinimide (NHS) ester of compound 1 (0.15 mg) was mixed with Avidin (1 mg) in 1 ml of PBS buffer and allowed to react for 1 hr. The reaction was purified by centrifuge through a Centriprep filter with a 10,000 molecular weight cutoff and the covalently bound dye was measured by a fluorimeter to show maximum excitation at 635 nm and maximum emission at 751 nm with a Stoke shift of 116 nm. The tricarbocyanine-amine-functionalized dye labeled avidin was mixed with biotin-labeled-Bombesin and evaluated by polyacrylamide gel electrophoresis. The sample was imaged as before with a Kodak Image Station MM4000. As shown in FIG. 2, a control in the first lane 1 in which there was no biotin-labled-Bombesin and Lanes 2, 3, and 4 do contain biotin-labeled Bombesin complexed which formed a stable complex with the tricarbocyanine-amine-functionalized dye labeled avidin. This dye labeled avidin will form stabile fluorescent complexes with biomolecules labeled with biotin and can then be used for in-vitro or in-vivo studies to detect other biomolecules labeled with biotin.

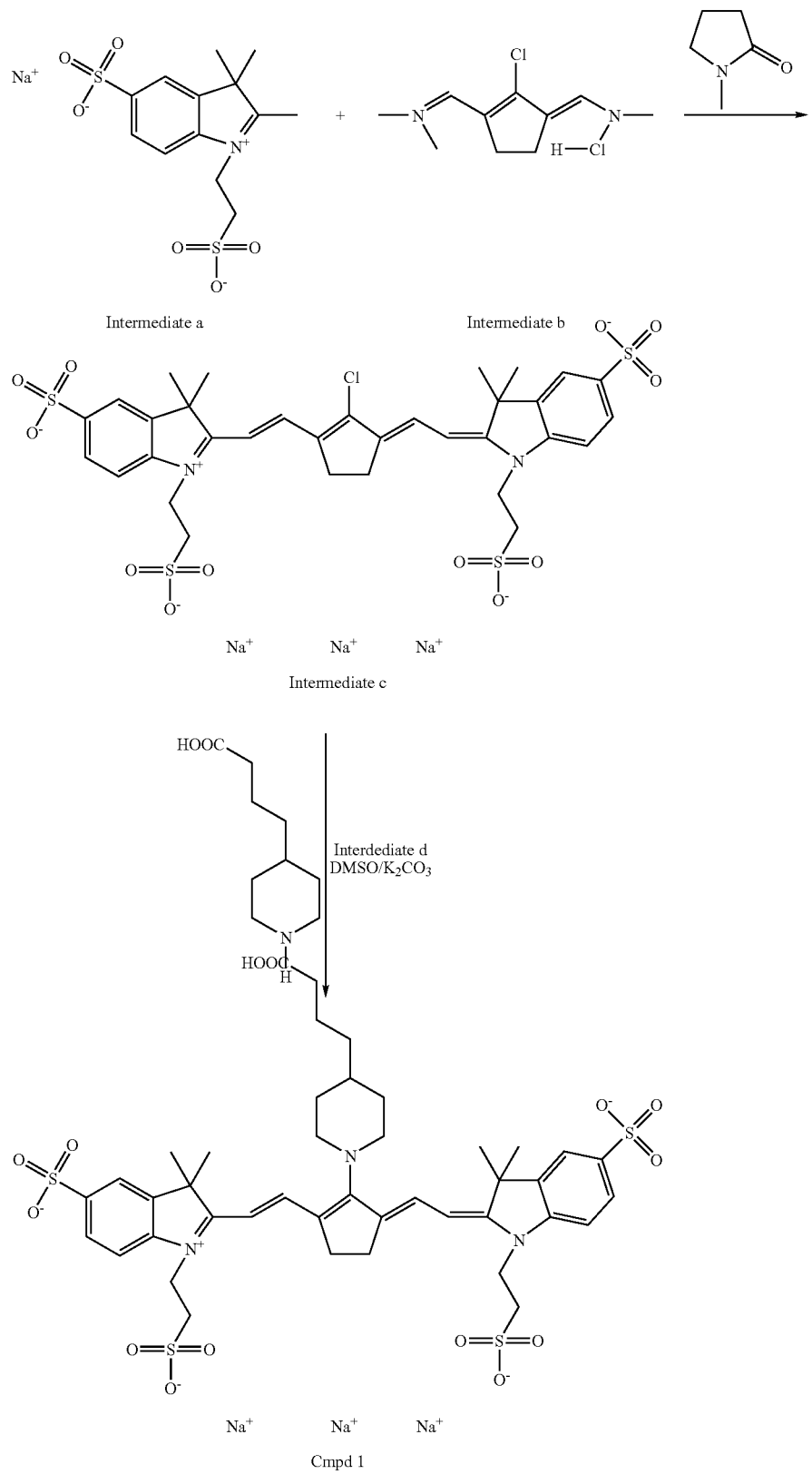

Intermediate b is prepared as described in U.S. Pat. No. 5,164,291, incorporated herein by reference. Col. 6, lines 15-30. Dimethylformamide (40 mL) and 40 mL dichloromethane were mixed and cooled to 5° C. Phosphorous oxychloride (37 mL) was dissolved in 40 mL dichloromethane and added dropwise to the dimethylformamide/dichloromethane solution at rate to maintain the temperature below 25° C. Cyclopentanone (8.8 g, 0.104 mol) was added and the mixture heated to reflux for 3 hours. After cooling to room temperature, the reaction mixture was poured into 200 mL of ice and allowed to sit overnight. The quenched reaction mixture was filtered twice to remove tarry by-products, then treated with sodium carbonate until the mixture was neutral. The resulting brown precipitate was collected by filtration, water washed, and dried to give 12.20 g blue-violet solid, mp 90°-94° C., $\lambda_{max}$=425 nm ($\epsilon$=38,000).

To a stirred solution of Intermediate a (14.6 g, 40 mmol) in N-methylpyrrolidone (80 ml) was added Intermediate b (5 g, 20 mmol). The resulting mixture was heated at 60 C for 5 hours. The mixture was poured into acetone after cooling to room temperature. The solid was collected and washed with more acetone. The crude dye C (11 g) was obtained and used directly in the next step.

A mixture of Intermediate c (3.6 g, 4 mmol), Intermediate d (1.7 g, 8 mmol), and $K_2CO_3$ (1.5 g) in dimethylsulfoxide (DMSO) (80 ml) was heated at 80 C for 6 hours. The cooled solution was poured into ether (400 ml), and the sticky solid was washed with acetone. Crude solid product Compound 1 (3.2 g) was obtained. The final product was purified through HPLC. Absorption maximum (methanol): 665 nm; the extinction coefficient: 118493 l/mole cm.

Scheme 2 Synthesis of Compound 2

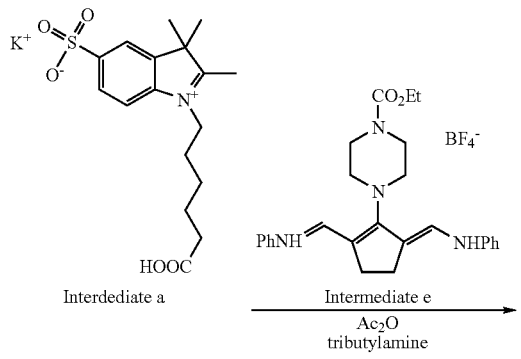

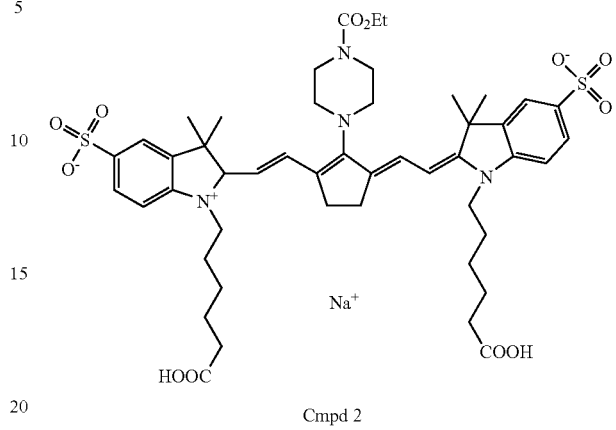

Cmpd 2

A mixture of Intermediate a (10 g, 20 mmol), Intermediate e (5.2 g, 10 mmol), acetic anhydride (100 ml) and tributylamine (6 g, 30 mmol) was heated to reflux for 6 hours. The resulting mixture was cooled to room temperature and then diluted with ether with stirring. The solvents were decanted from the oil and dissolved in water (5 ml) with sodium acetate (2 g). The mixture was heated to reflux for 5 minutes and then cooled. Isopropyl alcohol was then slowly added until a copper colored semi solid precipitated. The product (3.8 g) was obtained by decanting off the solvent, and dried overnight at 50 C in a high vacuum oven. The final product was purified through HPLC. Absorption maximum (methanol): 702 nm; the extinction coefficient: 125968 l/mole cm.

Comparision Data

As seen from the following chart many commercially available carbocyanine dyes have Stoke Shifts that are less than 40 nm.

| Dye | Source | Solvent | Absorbance Wavelength (nm) | Emission Wavelength (nm) | Stoke shift (nm) |
|---|---|---|---|---|---|
| Cy3 mono NHS ester | GE Healthcare | PBS | 548 | 562 | 14 |
| Cy5 mono NHS ester | GE Healthcare | PBS | 646 | 665 | 19 |
| Cy5.5 mono NHS Ester | GE Healthcare | PBS | 674 | 692 | 18 |
| Cy7 mono NHS ester | GE Healthcare | PBS | 747 | 774 | 27 |
| IR-768 | Sigma Aldrich | Methanol | 767 | 786 | 19 |
| Cresyl Violet | Sigma Aldrich | Methanol | 593 | 620 | 27 |
| Atto 520 | Sigma Aldrich | water | 520 | 542 | 22 |

| Dye | Source | Solvent | Absorbance Wavelength (nm) | Emission Wavelength (nm) | Stoke shift (nm) |
|---|---|---|---|---|---|
| Atto 565 | Sigma Aldrich | water | 561 | 585 | 24 |
| Atto 590 | Sigma Aldrich | water | 598 | 634 | 36 |
| Atto 610 | Sigma Aldrich | water | 605 | 646 | 41 |
| Atto 655 | Sigma Aldrich | water | 665 | 690 | 25 |
| Atto 680 | Sigma Aldrich | water | 680 | 702 | 22 |
| Alexa Fluor 555 | Invitrogen | n/a* | 555 | 565 | 10 |
| Alexa Fluor 633 | Invitrogen | n/a* | 632 | 647 | 15 |
| Alexa Fluor 647 | Invitrogen | n/a* | 650 | 665 | 15 |
| Alexa Fluor 660 | Invitrogen | n/a* | 663 | 690 | 27 |
| Alexa Fluor 680 | Invitrogen | n/a* | 679 | 702 | 23 |
| Alexa Fluor 700 | Invitrogen | n/a* | 702 | 723 | 21 |
| Alexa Fluor 750 | Invitrogen | n/a* | 749 | 775 | 26 |

*Manufacturer's data for N-hydroxysuccinimdyl esters (solvent not specified) taken from, Berlier et al., J. Histochem. & Cytochem., Vol. 51(12), p. 1703 (2003)

More Comparative Data

Many substituted carbocycanines do not give Stoke Shifts greater than 50 nm. Compounds A-K were synthesized by the methods known to those of ordinary skill in the art and described in F. M. Hamer "Heterocyclic Compounds-Cyanine Dyes and Related Topics", John Wiley and Sons, New York and London, pp. 245-269, 1964; and D. M. Stunner, "Heterocyclic Compounds-Special Topics in heterocylic chemistry", Chapter 18 and 14, pp. 485-515, John Wiley and Sons, New York and London, 1977.

| Dye | Solvent | Max Excitation (nm) | Max Emission (nm) | Stoke Shift (nm) |
|---|---|---|---|---|
| Compound A | Methanol | 824 | 849 | 25 |
| Compound B | Methanol | 800 | 819 | 19 |
| Compound C | Methanol | 792 | 812 | 20 |
| Compound D | Methanol | 796 | 826 | 30 |
| Compound E | Methanol | 803 | 824 | 21 |
| Compound F | Methanol | 821 | 842 | 21 |
| Compound G | Methanol | 802 | 846 | 44 |
| Compound H | Methanol | 802 | 844 | 42 |
| Compound I | Methanol | 782 | 803 | 21 |
| Compound J | Methanol | 787 | 807 | 20 |
| Compound K | Methanol | 794 | 820 | 26 |

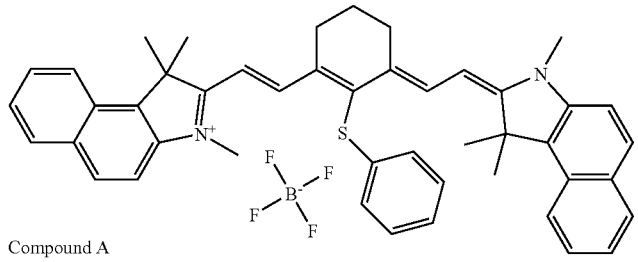

Compound A

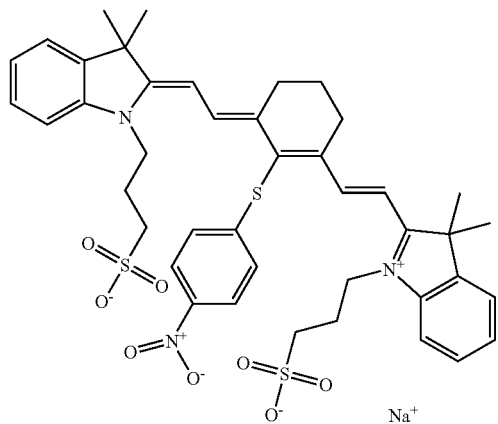
Compound B
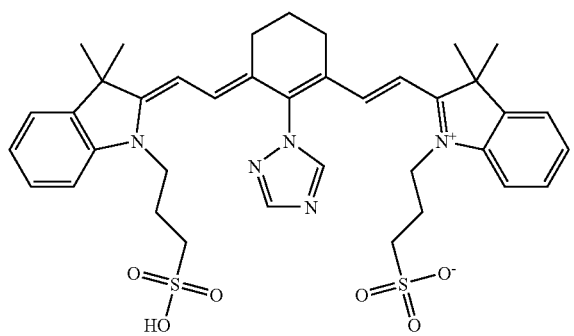
Compound C
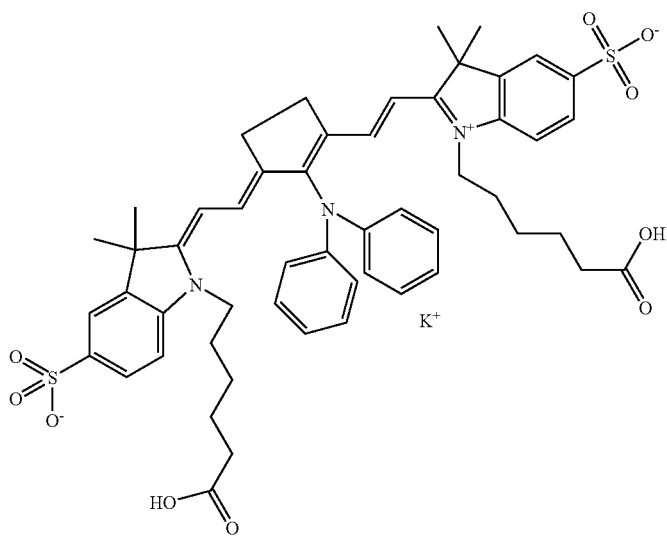
Compound D

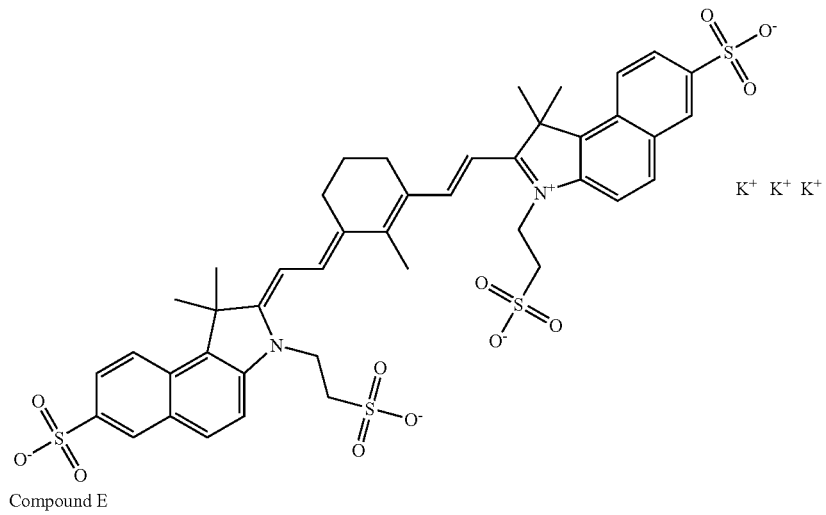
Compound E
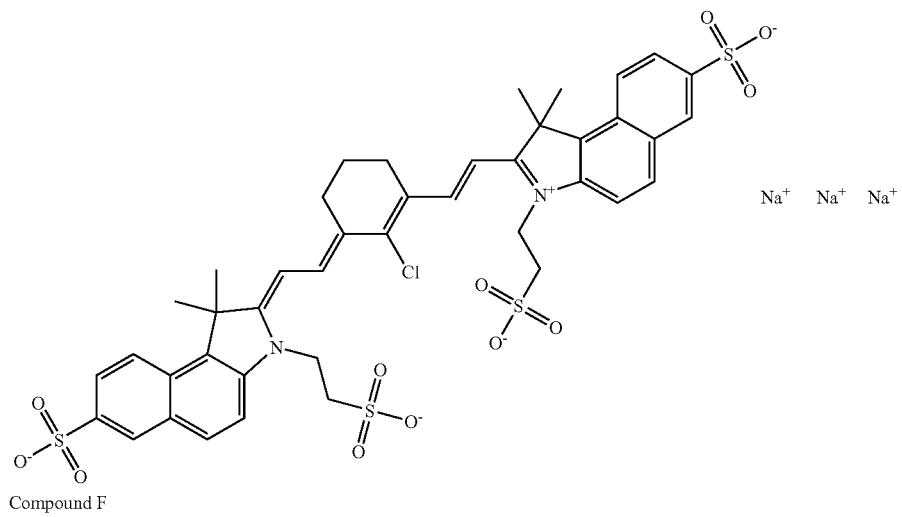
Compound F
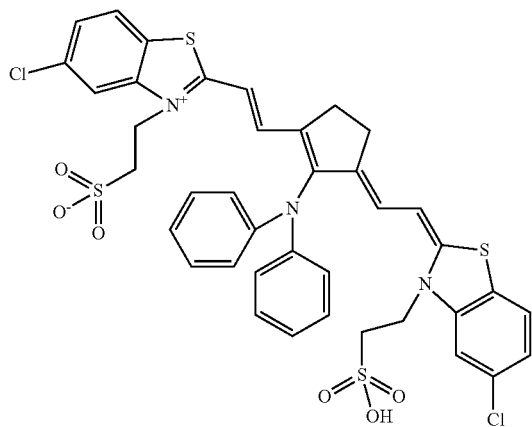

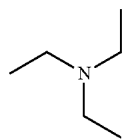
Compound G
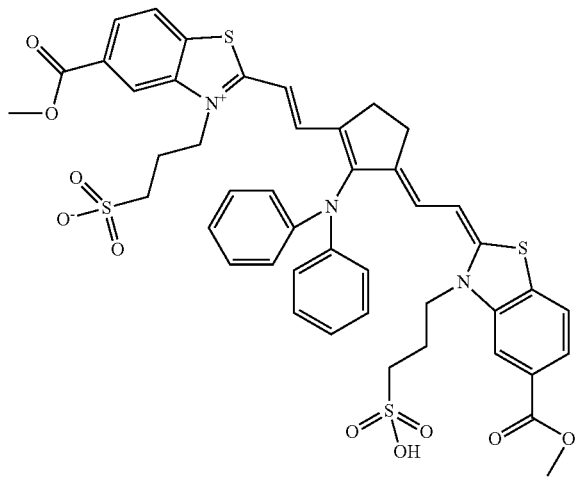
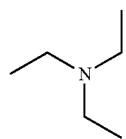
Compound H
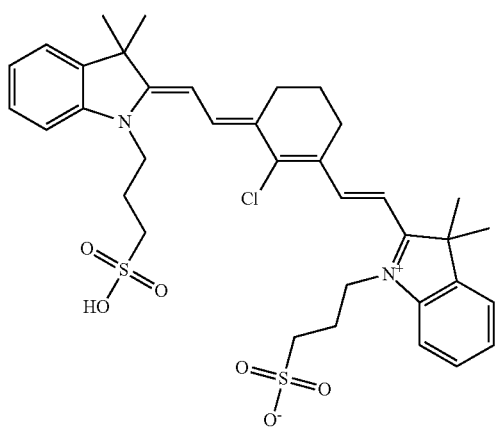

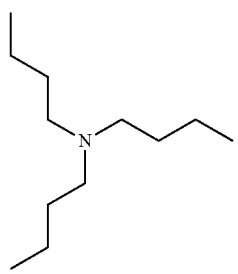
Compound I
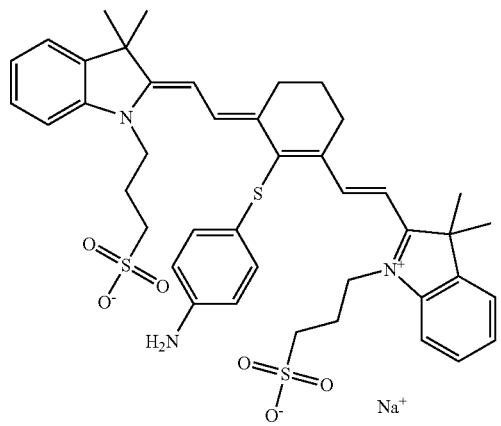
Compound J
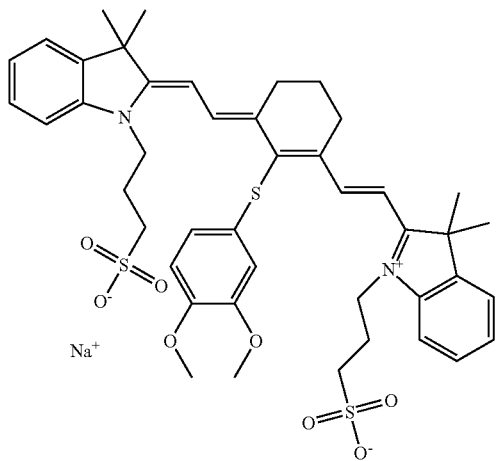
Compound K
Inventive Data: Table Showing Tricarbocyanine-Enamine-Functionalized Dyes which Have Stoke Shifts Greater than 50 nm
| Dye | Solvent | Max Excitation (nm) | Max Emission (nm) | Stoke Shift (nm) |
| --- | --- | --- | --- | --- |
| Compound 1 | H$_2$O (PBS) | 641 | 779 | 138 |
| Compound 2 | H$_2$O (PBS) | 689 | 796 | 107 |
| Compound 3 | H$_2$O (PBS) | 684 | 813 | 129 |
| Compound 4 | H$_2$O (PBS) | 721 | 813 | 92 |
| Compound 5 | H$_2$O (PBS) | 658 | 781 | 102 |

-continued
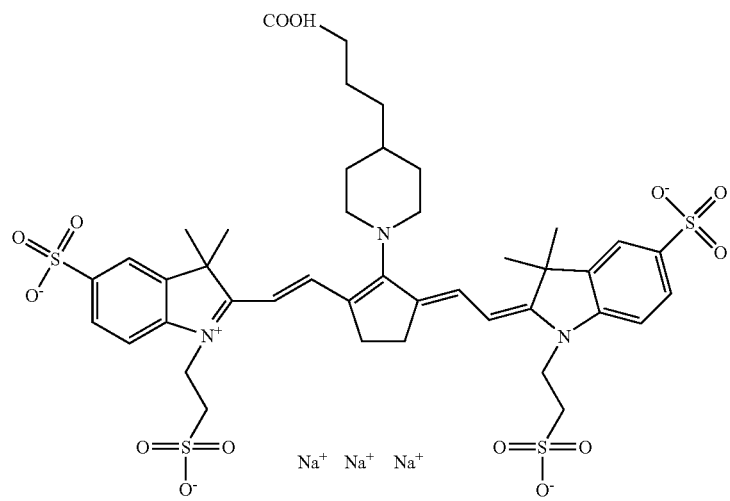
Compound 1
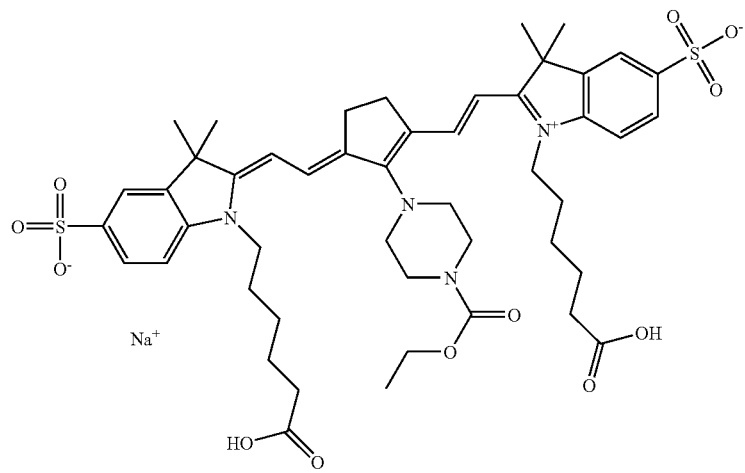
Compound 2
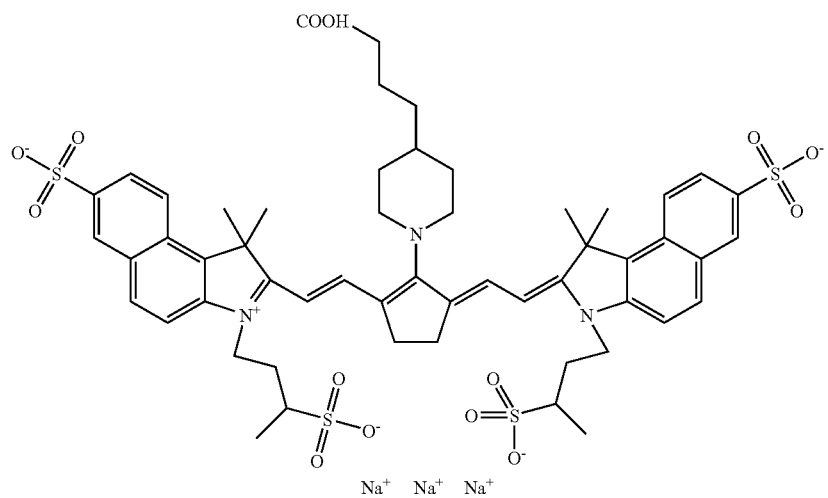
Compound 3

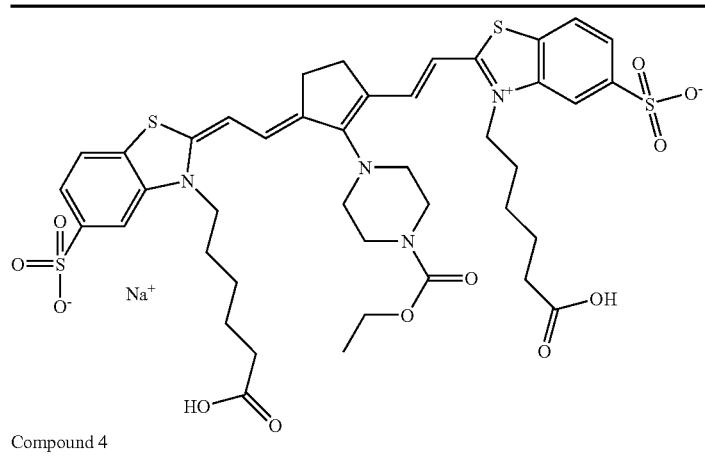
Compound 4

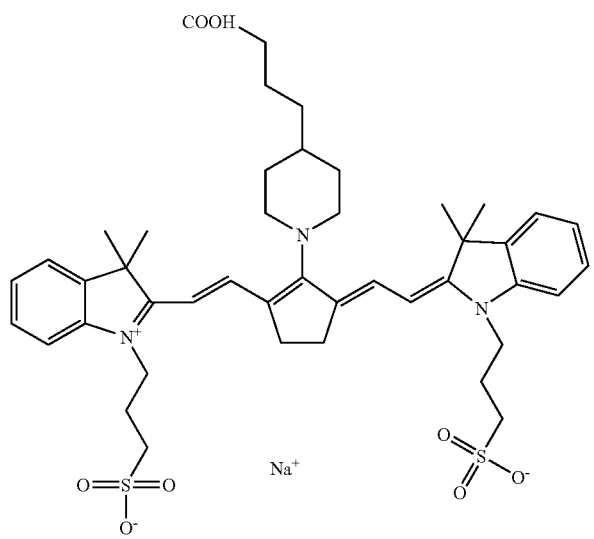
Compound 5

| Dye | Solvent | Max Excitation (nm) | Max Emission (nm) | Stoke Shift (nm) |
|---|---|---|---|---|
| Compound 1 | H$_2$O (PBS) | 641 | 779 | 138 |
| Compound 2 | H$_2$O (PBS) | 689 | 796 | 107 |
| Compound 3 | H$_2$O (PBS) | 684 | 813 | 129 |
| Compound 4 | H$_2$O (PBS) | 721 | 813 | 92 |
| Compound 5 | H$_2$O (PBS) | 658 | 781 | 102 |

The invention has been described in detail with particular reference to certain preferred embodiments thereof, but it will be understood that variations and modifications can be effected within the spirit and scope of the invention.

The invention claimed is:

1. A water dispersible, near-infrared tricarbocyanine, enamine-functionalized dye compound having a Stokes shift of greater than 50 nm and represented by at least one of the following five general formulae:

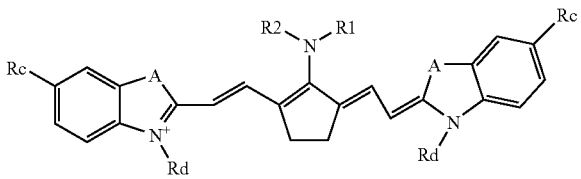

General Formula I wherein:

R1 and R2 are substituted alkyl groups and may together form a ring and at least one of R1 or R2 comprises a linking group selected from the group comprising COOH, NH2, maleimide, thiol, isocyanate, isothiocyanate, disulfide, alkynyl, azidoyl, or trialkoxysilane, wherein the linking group may form part of the ring;

A is Ra—C—Rb, wherein Ra and Rb are substituted or unsubstituted alkyl groups;

Rc is hydrogen or SO3-, aryl, alkyl, alkoxy, or halogen;

Rd is alkyl or (CH2)nSO3- where n=2 to 4,

General Formula II

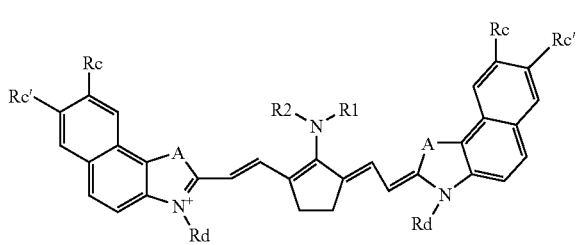

wherein:
R1 and R2 are substituted alkyl groups and are together capable of forming a ring, and at least one of R1 or R2 comprises a linking group selected from the group comprising COOH, NH2, maleimide, thiol, isocyanate, isothiocyanate, disulfide, alkynyl, azidoyl, or trialkoxysilane, wherein the linking group may form part of the ring;
A is Ra—C—Rb, wherein Ra and Rb are substituted or unsubstituted alkyl groups;
Rc is hydrogen or SO3-, aryl, alkyl, alkoxy, or halogen;
Rd is alkyl or (CH2)nSO3- where n=2 to 4, General Formula III

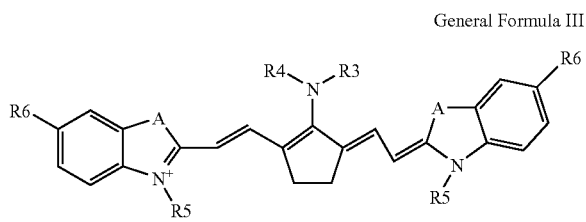

wherein:
A is Ra—C—Rb;
R3, R4, Ra, and Rb are substituted or unsubstituted alkyl groups capable of joining together to form a ring;
R6 is a SO3-;
R5 is a substituted alkyl group and at least one of the substituents is selected from the group comprising OH, NH2, COOH, maleimide, thiol, isocyante, isothiocyanate, disulfide, alkynyl, azidoyl, or trialkoxysilane;

General Formula IV

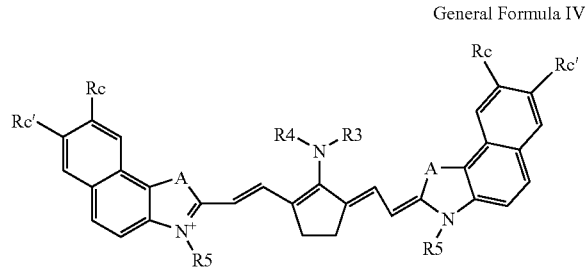

wherein:
A is Ra—C—Rb;
R3, R4, Ra, and Rb are substituted or unsubstituted alkyl groups capable of joining together to form a ring;
at least one of Rc and Rc' is a SO3-;
R5 is a substituted alkyl group and at least one of the substituents is selected from the group consisting of OH, NH2, COOH, maleimide, thiol, isocyante, isothiocyanate, disulfide, alkynyl, azidoyl, or trialkoxysilane;
Rc is hydrogen or SO3-, aryl, alkyl, alkoxy, or halogen; and General Formula V

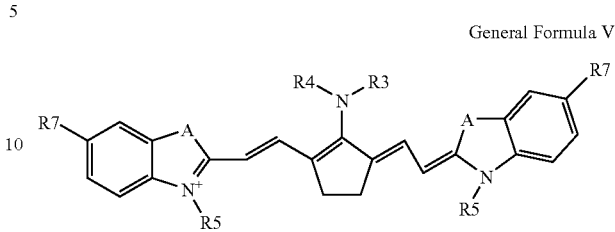

wherein:
A is Ra—C—Rb;
R3, R4, Ra, and Rb are substituted or unsubstituted alkyl groups capable of joining together to form a ring;
R7 is a COOH;
R5 is substituted alkyl and contains a SO3- group.

2. The water dispersible, near-infrared tricarbocyanine, enamine-functionalized dye compound of claim 1, wherein the dye compound comprises a carboxyethylpiperazine (enamine) bridging group.

3. The water dispersible, near-infrared tricarbocyanine, enamine-functionalized dye compound of claim 1 wherein Ra and Rb are methyl.

4. The water dispersible, near-infrared tricarbocyanine, enamine-functionalized dye compound of claim 1 wherein at least one of R1, R2, R3, R4 independently represents COOH.

5. The water dispersible, near-infrared tricarbocyanine, enamine-functionalized dye compound of claim 1 wherein said Stokes shift is from 70 to 140 nm.

6. The water dispersible, near-infrared tricarbocyanine, enamine-functionalized dye compound of claim 1 wherein said dye compound has a maximum excitation wavelength between 500 and 900 nm.

7. The water dispersible, near-infrared tricarbocyanine, enamine-functionalized dye compound of claim 1, wherein said dye compound has a maximum excitation wavelength between 500 and 900 nm and a Stokes shift of at least 70 nm.

8. The water dispersible, near-infrared tricarbocyanine, enamine-functionalized dye compound of claim 1, wherein said dye compound is:

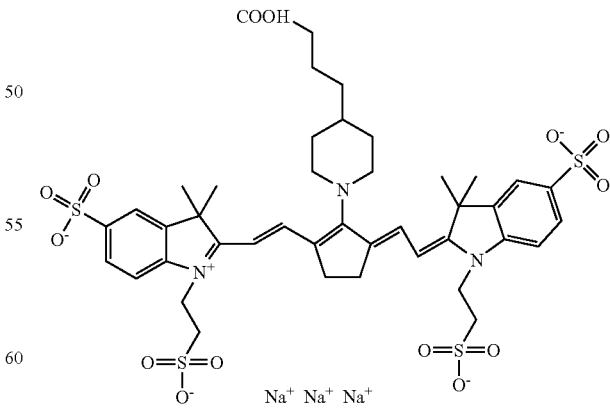

9. The water dispersible, near-infrared tricarbocyanine, enamine-functionalized dye compound of claim 1, wherein said dye compound is at least one member of the group represented by:

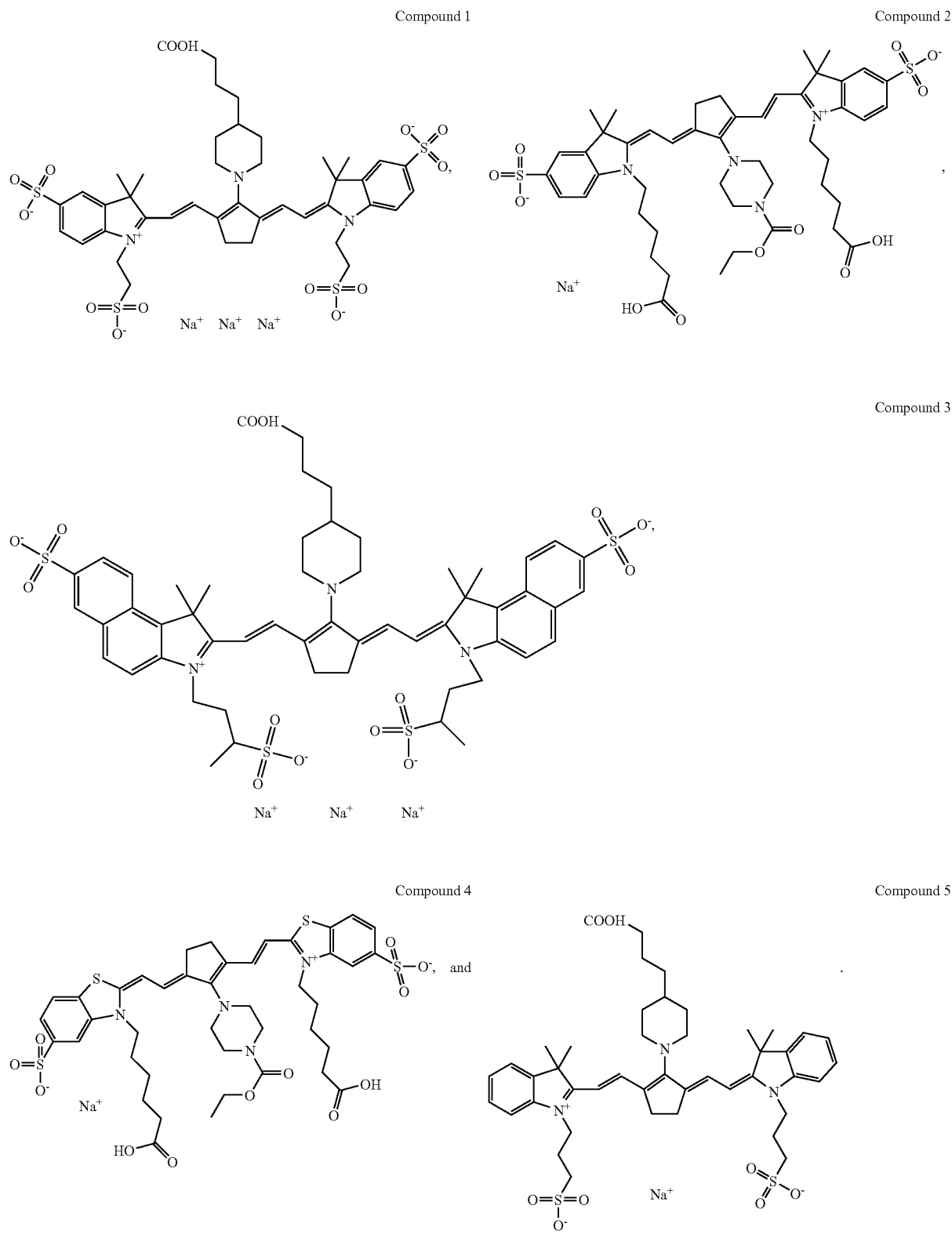

10. The water dispersible, near-infrared tricarbocyanine, enamine-functionalized dye compound of claim 1, wherein said dye compound is attached to biocompatible particles, biocompatible beads, microbeads or nanoparticles.

11. The water dispersible, near-infrared tricarbocyanine, enamine-functionalized dye compound of claim 1, wherein said dye compound is attached to peptides, proteins, antibodies or oligonucleotides.

12. The water dispersible, near-infrared tricarbocyanine, enamine-functionalized dye compound of claim 1, wherein said dye compound is attached to at least one drug.

13. The water dispersible, near-infrared tricarbocyanine, enamine-functionalized dye compound of claim 1, wherein said dye compound is attached to at least one cell.

14. The water dispersible, near-infrared tricarbocyanine, enamine-functionalized dye compound of claim 1 wherein said dye compound is attached to at least one non-biological material selected from the group consisting of soluble polymers, polymeric particles, glass and polymeric surfaces, and monomers.

* * * * *